(12) United States Patent
Lagrange et al.

(10) Patent No.: US 10,251,827 B2
(45) Date of Patent: *Apr. 9, 2019

(54) OXIDATION DYEING PROCESS USING A COMPOSITION COMPRISING A MONOAMINOBENZENE AND A METAL CATALYST

(71) Applicant: L'OREAL, Paris (FR)

(72) Inventors: Alain Lagrange, Coupvray (FR); Boris Lalleman, Paris (FR); Marie Mignon, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,653

(22) PCT Filed: Jun. 23, 2014

(86) PCT No.: PCT/EP2014/063174
§ 371 (c)(1),
(2) Date: Dec. 18, 2015

(87) PCT Pub. No.: WO2014/202787
PCT Pub. Date: Dec. 24, 2014

(65) Prior Publication Data
US 2016/0128922 A1 May 12, 2016

(30) Foreign Application Priority Data
Jun. 21, 2013 (FR) ...................... 13 55962

(51) Int. Cl.
*A61Q 5/10* (2006.01)
*A61K 8/41* (2006.01)
*A61K 8/365* (2006.01)
*A61K 8/19* (2006.01)
*A61K 8/22* (2006.01)
*A61K 8/49* (2006.01)

(52) U.S. Cl.
CPC ............... *A61K 8/411* (2013.01); *A61K 8/19* (2013.01); *A61K 8/22* (2013.01); *A61K 8/365* (2013.01); *A61K 8/494* (2013.01); *A61K 8/4946* (2013.01); *A61Q 5/10* (2013.01); *A61K 2800/4324* (2013.01); *A61K 2800/58* (2013.01); *A61K 2800/882* (2013.01); *A61K 2800/884* (2013.01)

(58) Field of Classification Search
CPC . A61Q 5/10; A61K 8/411; A61K 8/19; A61K 8/22; A61K 8/494; A61K 8/4946; A61K 2800/882; A61K 2800/884; A61K 2800/4324; A61K 2800/58
See application file for complete search history.

(56) References Cited

U.S. PATENT DOCUMENTS

| | | |
|---|---|---|
| 4,865,617 A | 9/1989 | Junino et al. |
| 6,572,664 B2 | 6/2003 | Breton et al. |
| 7,776,107 B2 | 8/2010 | Vidal et al. |
| 7,927,383 B2 | 4/2011 | Hercouet et al. |
| 2002/0002749 A1 | 1/2002 | Breton et al. |
| 2002/0034488 A1 | 3/2002 | Kravtchenko et al. |
| 2003/0066140 A1* | 4/2003 | Bartolone ............... A61K 8/19 8/405 |
| 2005/0005370 A1 | 1/2005 | Lim et al. |
| 2010/0154136 A1* | 6/2010 | Hercouet ................. A61K 8/31 8/406 |
| 2010/0154140 A1* | 6/2010 | Simonet .................. A61K 8/31 8/416 |
| 2010/0154143 A1 | 6/2010 | Guerin |
| 2010/0180389 A1 | 7/2010 | Hercouet et al. |

FOREIGN PATENT DOCUMENTS

CN 101744736 6/2010
EP 0657158 A1 6/1995
(Continued)

OTHER PUBLICATIONS

STIC Search Report dated May 17, 2016.*
(Continued)

*Primary Examiner* — Eisa B Elhilo
(74) *Attorney, Agent, or Firm* — The Marbury Law Group, PLLC

(57) ABSTRACT

The invention relates to a process for dyeing keratin fibers, comprising the use of one or more metal catalysts and of a composition (A) comprising: —one or more oxidizing agents, and —at least one monoaminobenzene of formula (I), or an addition salt or solvate thereof in which the radicals R1 to R5 represent, independently of each other: a hydrogen atom; a halogen atom, a C1-C6 alkyl radical, a C1-C6 alkoxy radical, a carboxylic radical (—COOH), a sulfonic radical (—S03 H); two of the adjacent radicals R1 to R5 possibly forming, with the carbon atoms that bear them, a saturated or unsaturated 5- to 7-membered ring, optionally comprising from 1 to 2 heteroatoms, preferably oxygen, the said ring being optionally fused with a saturated or unsaturated 5- to 6-membered ring; on condition that at least one of the radicals R1 to R5 represents an optionally substituted alkoxy radical and preferably at least one of the other radicals R1 to R5 is a hydrogen atom.

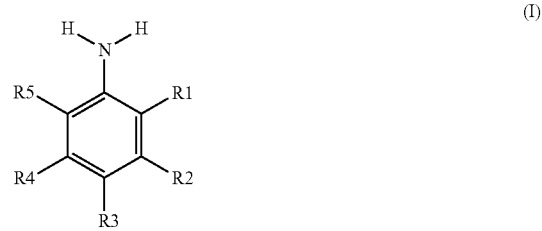

(I)

18 Claims, No Drawings

(56) References Cited

FOREIGN PATENT DOCUMENTS

| EP | 1157684 | A2 | 11/2001 |
|---|---|---|---|
| FR | 2603483 | A1 | 3/1988 |
| FR | 2735976 | A1 | 1/1997 |
| FR | 2763841 | A1 | 12/1998 |
| FR | 2830193 | A1 | 4/2003 |
| JP | S63-68670 | A | 3/1988 |
| JP | 2010-138173 | A | 6/2010 |
| JP | 2010-143916 | A | 7/2010 |
| WO | 2014/202792 | A2 | 12/2014 |

OTHER PUBLICATIONS

Todd, Charles, et al., "Volatile Silicone Fluids for Cosmetic Formulations," Cosmetics and Toiletries, vol. 91, Jan. 1976, pp. 29-32.
English language Abstract for EP 0657158A1 (Jun. 14, 1995).
Machine generated English language Abstract for FR 2735976A1 (Jan. 3, 1997).
English language Abstract for FR 2763841A1 (Dec. 4, 1998).
International Search Report for PCT/EP2014/063174, dated Oct. 6, 2014.
International Search Report for PCT/EP2014/063181, dated Apr. 7, 2015.
Boruszczak, Z. et al., "Synthesis of 5-nitro- and 5-aminobenzimidazolone-2," Dyes and Pigments, vol. 40, No. 2-3, (Jan. 19, 1999), pp. 261-264.
Non-Final Office Action for co-pending U.S. Appl. No. 14/899,605 (dated Nov. 9, 2016).
Office Action for counterpart CN Application No. 201480034300.X dated Jan. 17, 2018.
Office Action for counterpart CN Application No. 201480034300 dated Feb. 23, 2017.
Final Office Action for copending U.S. Appl. No. 14/899,605, dated Jun. 7, 2017. (now Abandoned).

* cited by examiner

OXIDATION DYEING PROCESS USING A COMPOSITION COMPRISING A MONOAMINOBENZENE AND A METAL CATALYST

CROSS REFERENCE TO RELATED APPLICATIONS

This is a national stage application of PCT/EP2014/063174, filed internationally on Jun. 23, 2014, which claims priority to French Application No. 1355962, filed on Jun. 21, 2013, both of which are incorporated by reference herein in their entireties.

The present invention relates to a process for dyeing keratin fibres, comprising one or more metal catalysts.

Many people have sought for a long time to modify the colour of their hair and in particular to mask their grey hair.

It is known practice to obtain "permanent" or oxidation colorations with dye compositions containing oxidation dye precursors, which are generally known as oxidation bases, such as ortho- or para-phenylenediamines, ortho- or para-aminophenols and heterocyclic compounds. These oxidation bases are initially colourless or weakly coloured compounds, which, when combined with oxidizing products, may give rise to coloured compounds via a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds, such as indole compounds. The variety of molecules used as oxidation bases and couplers allows a wide range of colours to be obtained.

The permanent dyeing process thus consists in applying, to the keratin fibres, bases or a mixture of bases and couplers with hydrogen peroxide ($H_2O_2$ or aqueous hydrogen peroxide solution), as oxidizing agent, in leaving to diffuse, and in then rinsing the fibres. The colorations which result therefrom have the advantage of being permanent, strong and resistant to external agents, in particular to light, bad weather, washing operations, perspiration and rubbing actions.

However, it is still sought to increase the efficiency of the reaction of the oxidation dyes used during this process in order to improve their build-up on keratin fibres. Indeed, such an improvement would make it possible in particular to decrease the contents of the oxidation dyes present in dyeing compositions, to reduce the leave-on time on keratin fibres and/or to use other dye families which have a weak dyeing capacity but which are capable of exhibiting a good toxicological profile, of providing new shades or of producing colorations which are resistant with respect to external agents such as light or shampoos.

In this regard, it has already been proposed to use cosmetic compositions containing metal catalysts during a dyeing process in order to accelerate the dye oxidation reaction and to improve the intensity of the coloration on the keratin fibres. However, the dyeing power obtained is still not entirely satisfactory and the colorations obtained are generally too selective, i.e. these colorations are not uniform along the keratin fibre.

There is therefore a real need to provide a process for dyeing keratin fibres which is carried out in the presence of an oxidizing agent and which does not have the drawbacks of the existing processes, i.e. which is capable of resulting in a satisfactory intensity of the oxidation dyes on the keratin fibres while at the same time resulting in relatively non-selective colorations.

This aim is achieved by the present invention, one subject of which is especially a process for dyeing keratin fibres, in particular human keratin fibres such as the hair, comprising the use of one or more metal catalysts and of a composition (A) comprising:

(a) at least one oxidizing agent, and
(b) at least one monoaminobenzene of formula (I) below, or an addition salt or solvate thereof

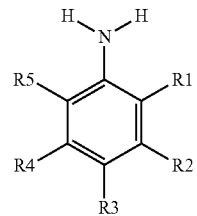

(I)

in which the radicals R1 to R5 represent, independently of each other:

a hydrogen atom;
a halogen atom, preferably chosen from F, Cl and Br;
a linear or branched C1-C6 and preferably C1-C4 alkyl radical, which is optionally substituted, preferably with one or more OH, NH2, CN, COOH or amino(C1-C4) alkoxyphenyl groups, preferably OH;
a linear or branched C1-C6 and preferably C1-C4 alkoxy radical, which is optionally substituted, preferably with one or more OH, NH2, di(C1-C4)alkylamino, CN, CF3, aminophenoxy, C1-C4 hydroxyalkoxy, C1-C4 alkoxy or pyrrolidine groups;
a carboxylic (—COOH) or sulfonic (—SO3H) radical;
two of the adjacent radicals R1 to R5 possibly forming, with the carbon atoms that bear them, a saturated or unsaturated, 5- to 7-membered ring, optionally comprising from 1 to 2 heteroatoms, preferably oxygen, the said ring being optionally fused with a saturated or unsaturated 5- to 6-membered ring; and
on condition that at least one of the radicals R1 to R5 represents an optionally substituted alkoxy radical and preferably at least one of the other radicals is a hydrogen atom.

Preferably, in formula (I) above, at least one of the radicals R1 to R5 is an optionally substituted alkoxy radical, at least one other is an alkoxy or alkyl radical or forms, with an adjacent radical and the carbon atoms to which they are attached, a ring, and the other radicals are hydrogen atoms.

A subject of the invention is also a hair dye composition comprising one or more oxidation bases of formula (I) and at least 10% and preferably at least 20% of fatty substances, and also the use of this composition for dyeing keratin fibres, especially the hair.

The dyeing process according to the invention produces a satisfactory colour intensity on keratin fibres while at the same time being sparingly selective, i.e. giving homogeneous colorations along the keratin fibre. Furthermore, the process according to the present invention makes it possible to produce strong and chromatic colorations.

Moreover, the dyeing process according to the invention makes it possible to improve the intensity of the coloration on the keratin fibres compared with a conventional dyeing process.

In the process of the invention, the metal catalyst(s) may constitute or form part of a composition (B) which may be mixed with composition (A) before applying the mixture to keratin fibres or applied separately as a pre-treatment or post-treatment with or without intermediate rinsing. It should be noted that composition (B) may consist solely of the metal catalyst(s).

The present invention also relates to a multi-compartment device comprising a first compartment containing a composition (B) comprising one or more metal catalysts, a second compartment containing a composition (A') comprising one or more oxidation dyes of formula (I), and a third compartment containing a composition (C) comprising one or more oxidizing agents. According to a particular embodiment, one or more fatty substances are present in at least one of the compositions (A') or (C) such that, after mixing together compositions (A') and (C), the content of fatty substances is greater than or equal to 10% by weight relative to the total weight of the mixture of compositions (A') and (C).

According to a particular embodiment, the device comprises a fourth compartment comprising a composition (D) comprising one or more fatty substances, the said composition (D) being intended to be mixed with compositions (A') and (C), the content of fatty substances preferably being greater than or equal to 10% by weight relative to the total weight of the mixture of compositions (A'), (C) and (D), composition (A') or (C) possibly containing one or more fatty substances.

Other characteristics and advantages of the invention will emerge more clearly on reading the description and the examples that follow.

In that which follows and unless otherwise indicated, the limits of a range of values are included in this range.

The expression "at least one" is equivalent to the expression "one or more".

The keratin fibres treated via the process according to the invention are preferably the hair.

The dyeing process according to the present invention uses one or more metal catalysts.

Metal catalysts are compounds that comprise one or more metals in their structure.

The metals are chosen from transition metals and rare-earth metals, and alloys thereof.

In particular, the metals are chosen from transition metals and rare-earth metals.

Among the transition metals, mention may be made especially of manganese, iron, cobalt, copper, zinc, platinum, nickel, titanium, silver, zirconium, chromium, molybdenum, tungsten, platinum, gold and vanadium, and among these most particularly manganese.

Among the rare-earth metals, mention may particularly be made of cerium.

Thus, the metal catalysts are especially catalysts based on transition metals or on rare-earth metals, and more particularly manganese-based, vanadium-based or cerium-based catalysts.

The metal catalysts used may be chosen from metal salts, metal oxides and metal complexes, and mixtures thereof and solvates thereof, including hydrates.

For the purposes of the present invention, the term "metal complexes" means systems in which the metal ion, i.e. the central atom, is bonded to one or more electron donors, called ligands, via chemical bonds.

Preferably, the metal catalysts used in the dyeing process are chosen from metal salts.

For the purposes of the present invention, the term "metal salts" means the salts derived from the action of an acid on a metal.

Preferentially, the metal catalysts used in the dyeing process are chosen from transition metal salts, such as manganese salts, and rare-earth metal salts, such as cerium salts, and also mixtures thereof.

The metal salts may be mineral or organic salts.

The inorganic metal salts may be chosen from halides, carbonates, sulfates and phosphates, especially hydrated or anhydrous halides.

According to another preferred variant, the metal salts are in oxidation state II and bear two (poly)hydroxy acid-based ligands.

The term "(poly)hydroxy acid" means any carboxylic acid which comprises a hydrocarbon-based chain which is linear or branched, and saturated or unsaturated, preferably saturated and/or linear, comprising from 1 to 10 carbon atoms and from 1 to 9 hydroxyl groups, and comprising from 1 to 4 carboxylic groups —C(O)—OH, at least one of the said —C(O)—OH functions of which is in the carboxylate form —C(O)—O— complexed with the metal atom, preferably Mn(II). More particularly, the metal salt is complexed with two carboxylate groups such as that of formula (II):

and also the solvates thereof, such as hydrates, and enantiomers thereof, in which formula (II):

M represents a metal (II) or metal2+ in oxidation state 2,

R and R', which may be identical or different, represent a (C1-C6)(poly)hydroxyalkyl group.

The metal catalysts are particularly chosen from organic acid salts of transition metals, especially of manganese, and mineral salts of rare-earth metals, especially of cerium.

According to a particular embodiment of the invention, the manganese is a manganese salt.

The organic metal salts may be more particularly chosen from organic acid salts such as citrates, lactates, glycolates, gluconates, acetates, propionates, fumarates, oxalates and tartrates, especially gluconates.

More preferentially, the metal catalysts are chosen from manganese gluconate and cerium chloride heptahydrate, in particular manganese gluconate.

Preferably, the metal catalyst(s) are chosen from the compounds of formula (II) and more particularly represent manganese gluconate.

Preferentially, the metal catalysts are chosen from organic acid salts of transition metals, especially of manganese, and mineral salts of rare-earth metals, especially of cerium.

Composition B may exclusively contain the metal catalyst(s). This composition may also contain other compounds. This composition B may be anhydrous or aqueous.

The metal catalysts, after mixing with composition (A), may be present in a content ranging from 0.001% to 10% by weight, preferably in a content ranging from 0.001% to 1% by weight, better still ranging from 0.01% to 0.5% by weight relative to the total weight of the final composition after mixing with the oxidizing agent(s).

As indicated previously, the dyeing process of the invention uses a composition (A) which may comprise one or more fatty substances.

The term "fatty substance" means an organic compound that is insoluble in water at ordinary room temperature (25° C.) and at atmospheric pressure (760 mmHg) (solubility of less than 5%, preferably less than 1% and even more preferentially less than 0.1%). They have in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

These fatty substances are neither polyoxyethylenated nor polyglycerolated. They are different from fatty acids since salified fatty acids constitute soaps which are generally soluble in aqueous media.

The fatty substances are in particular chosen from $C_6$-$C_{16}$ hydrocarbons or hydrocarbons comprising more than 16 carbon atoms and in particular alkanes, oils of animal origin, oils of plant origin, fluoro oils or glycerides of synthetic origin, fatty alcohols, fatty acid and/or fatty alcohol esters, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular with one or more (in particular 1 to 4) hydroxyl groups. If they are unsaturated, these compounds may comprise one to three conjugated or non-conjugated carbon-carbon double bonds.

As regards the $C_6$-$C_{16}$ alkanes, they are linear or branched, and possibly cyclic. Examples that may be mentioned include hexane, dodecane, undecane, tridecane, and isoparaffins, for instance isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, jojoba oil, shea butter oil, caprylic/capric acid triglycerides, for instance those sold by the company Stéarineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-(trifluoromethyl)perfluoromorpholine sold under the name PF 5052® by the company 3M.

The fatty alcohols that may be used in the cosmetic composition (E) are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in composition (A) are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and in particular mono- or di-oleate, -stearate, -behenate, oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar of fatty acid that may also be mentioned include:
- the products sold under the names F160, F140, F110, F90, F70 and SL40 by the company Crodesta, respectively denoting sucrose palmitate/stearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referenced B370 and corresponding to sucrose behenate formed from 20% monoester and 80% diester-triester-polyester;
- the sucrose monopalmitate/stearate-dipalmitate/stearate sold by the company Goldschmidt under the name Tegosoft® PSE.

The silicones that may be used in the cosmetic composition (I) of the present invention are volatile or non-volatile, cyclic, linear or branched silicones, which are unmodified or modified by organic groups, having a viscosity from $5 \times 10^{-6}$ to 2.5 m²/s at 25° C., and preferably $1 \times 10^{-5}$ to 1 m²/s.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's *Chemistry and Technology of Silicones* (1968), Academic Press. They may be volatile or nonvolatile.

When they are volatile, the silicones are more particularly chosen from those with a boiling point of between 60° C. and 260° C., and even more particularly from:
(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and also mixtures thereof.

Mention may also be made of cyclocopolymers of the dimethylsiloxane/methylalkylsiloxane type, such as Volatile Silicone® FZ 3109 sold by the company Union Carbide, of formula:

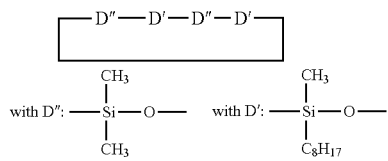

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use is preferably made of non-volatile polydialkylsiloxanes, polydialkylsiloxane gums and resins, polyorganosiloxanes modified with the organofunctional groups above, and also mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 mm²/s;
- the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that can be used more particularly in accordance with the invention are mixtures such as:
  mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning;
  mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
  mixtures of two PDMSs with different viscosities, and more particularly of a PDMS gum and of a PDMS oil, such as the product SF 1236 from the company General Electric. The product SF 1236 is a mixture of a gum SE 30 defined above, with a viscosity of 20 $m^2/s$ and of an oil SF 96 with a viscosity of $5 \times 10^{-6}$ $m^2/s$. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, and which are silicones of dimethyl/trimethylsiloxane structure.

Mention may also be made of the trimethyl siloxysilicate-type resins sold in particular under the names X22-4914, X21-5034 and X21-5037 by the company Shin-Etsu.

The organomodified silicones that may be used in accordance with the invention are silicones as defined previously and comprising in their structure one or more organofunctional groups attached via a hydrocarbon-based group.

Besides the silicones described above, the organomodified silicones may be polydiarylsiloxanes, in particular polydiphenylsiloxanes, and polyalkylarylsiloxanes functionalized by the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ $m^2/s$ at 25° C.

Among these polyalkylarylsiloxanes, examples that may be mentioned include the products sold under the following names:
  the Silbione® oils of the 70 641 series from Rhodia;
  the oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Among the organomodified silicones, mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$-$C_4$ amino alkyl groups;
  alkoxy groups such as the product sold under the name Silicone Copolymer F-755 by SWS Silicones, and Abil Wax® 2428, 2434 and 2440 by the company Goldschmidt.

The fatty substances are advantageously chosen from $C_6$-$C_{16}$ hydrocarbons or hydrocarbons comprising more than 16 carbon atoms, and in particular alkanes, oils of plant origin, fatty alcohols, fatty acid and/or fatty alcohol esters, and silicones, or mixtures thereof.

Preferably, the fatty substance is an oil (a compound that is liquid at a temperature of 25° C. and at atmospheric pressure).

Preferably, the fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof. Better still, the fatty substance is chosen from liquid petroleum jelly, $C_6$-$C_{16}$ alkanes and polydecenes.

Preferably, the fatty substances are present in a content of greater than or equal to 10% by weight relative to the total weight of the cosmetic composition (A).

Thus, according to a particular embodiment, composition (A) has a content of fatty substances, preferably of oils, preferably ranging from 10% to 70% by weight, even more particularly ranging from 25% to 70% by weight, better still from 25% to 60% by weight and most particularly from 30% to 60% by weight relative to the total weight of composition (A).

The invention uses a monoaminobenzene of formula (I).

Examples of monoaminobenzenes of formula (I) that may be mentioned include the following oxidation bases, salts thereof and solvates thereof:

1) Para-Aminobenzene Oxidation Bases

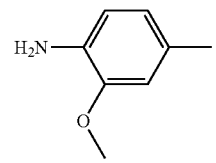

2-methoxy-4-methylaniline 39538-68-6

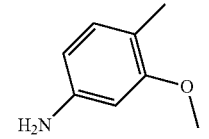

3-methoxy-4-methylaniline 16452-01-0

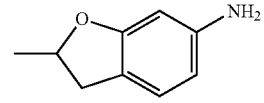

2-methyl-2,3-dihydrobenzofuran-6-amine 129014-10-4

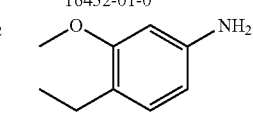

4-ethyl-3-methoxybenzenamine 947691-59-0

-continued

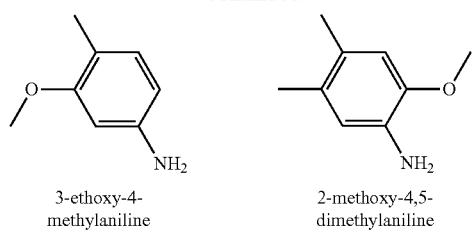

3-ethoxy-4-
methylaniline

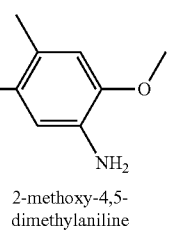

2-methoxy-4,5-
dimethylaniline

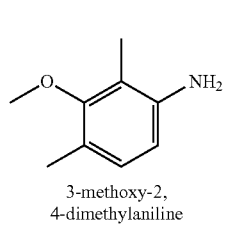

3-methoxy-2,
4-dimethylaniline

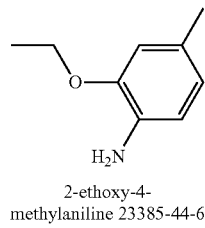

2-ethoxy-4-
methylaniline 23385-44-6

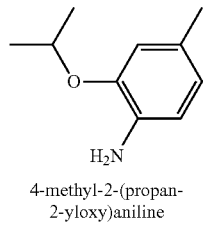

4-methyl-2-(propan-
2-yloxy)aniline

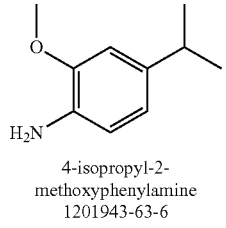

4-isopropyl-2-
methoxyphenylamine
1201943-63-6

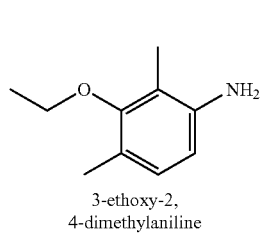

3-ethoxy-2,
4-dimethylaniline

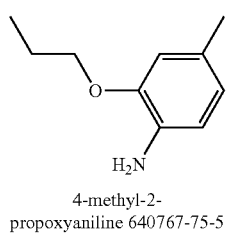

4-methyl-2-
propoxyaniline 640767-75-5

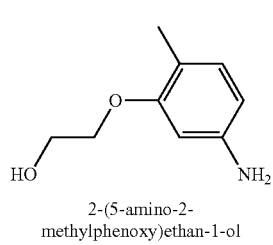

2-(5-amino-2-
methylphenoxy)ethan-1-ol

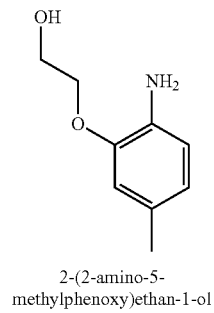

2-(2-amino-5-
methylphenoxy)ethan-1-ol

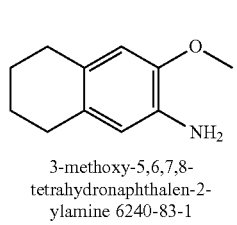

3-methoxy-5,6,7,8-
tetrahydronaphthalen-2-
ylamine 6240-83-1

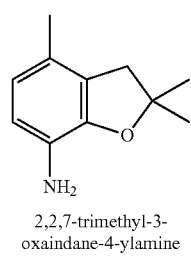

2,2,7-trimethyl-3-
oxaindane-4-ylamine

-continued

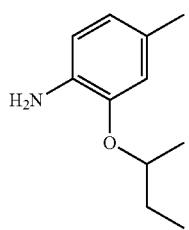

2-(butan-2-yloxy)-4-
methylaniline

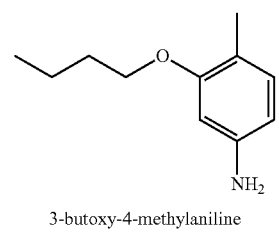

3-butoxy-4-methylaniline

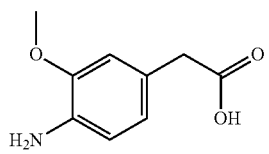

1-(4-amino-3-
methoxyphenyl)acetic acid
230648-62-1

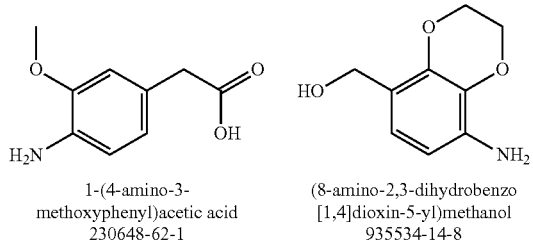

(8-amino-2,3-dihydrobenzo
[1,4]dioxin-5-yl)methanol
935534-14-8

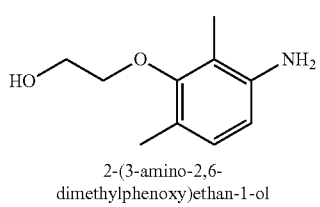

2-(3-amino-2,6-
dimethylphenoxy)ethan-1-ol

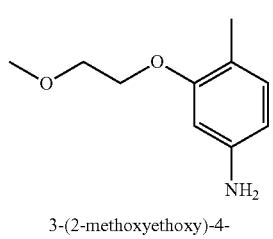

3-(2-methoxyethoxy)-4-
methylaniline

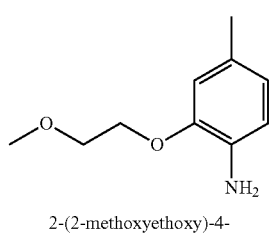

2-(2-methoxyethoxy)-4-
methylaniline 946716-14-9

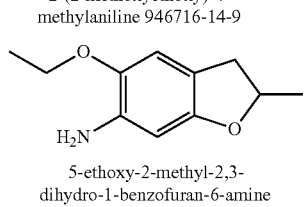

5-ethoxy-2-methyl-2,3-
dihydro-1-benzofuran-6-amine

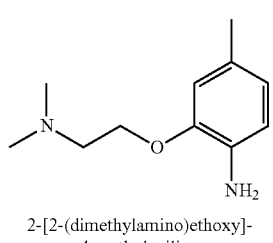

2-[2-(dimethylamino)ethoxy]-
4-methylaniline

-continued

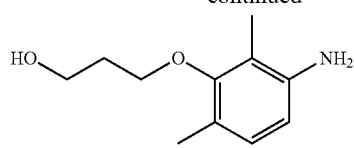

3-(3-amino-2,6-
dimethylphenoxy)propan-1-ol

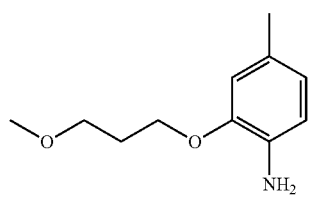

2-(3-methoxypropoxy)-4-
methylaniline 946716-26-3

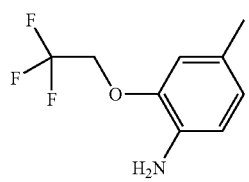

4-methyl-2-(2,2,2-
trifluoroethoxy)aniline

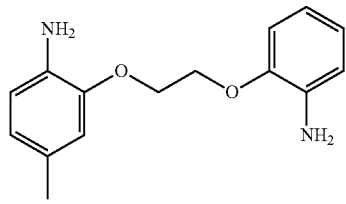

2-[2-(2-aminophenoxy)ethoxy]-4-
methyl-benzenamine 96331-95-2

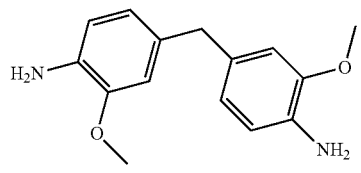

4-(4-amino-3-methoxybenzyl)-2-
methoxyaniline

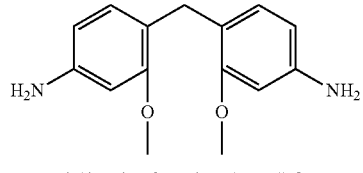

4-(4-amino-2-methoxybenzyl)-3-
methoxyaniline

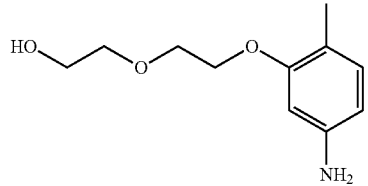

2-[2-(5-amino-2-
methylphenoxy)ethoxy]ethan-1-ol

2) Para-Aminobenzene Oxidation Bases:

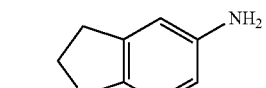

2,3-dihydro-1-benzofuran-
5-amine 42933-43-7

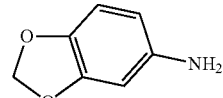

3,4-(methylenedioxy)aniline
14268-66-7

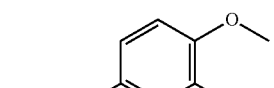

3-methyl-4-
methoxyaniline 136-90-3

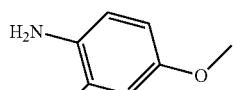

4-methoxy-2-
methylaniline 102-50-1

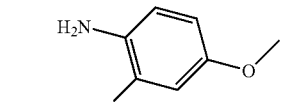

2-fluoro-4-methoxyaniline
458-52-6

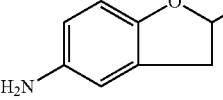

(2-methyl-2,3-dihydro-1-
benzofuran-5-yl)amine
26210-77-5

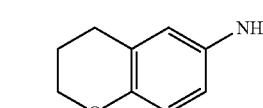

3-4-dihydro-2h-chromen-
6-amine

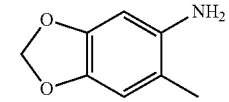

(6-methyl-1,3-
benzodioxol-5-yl)amine
62052-49-7

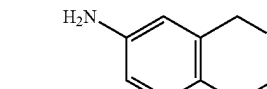

4,5-dihydro-1,3-benzodioxine-
6-amine 22791-64-6

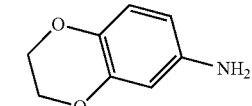

1,4-benzodioxan-6-amine
22013-33-8

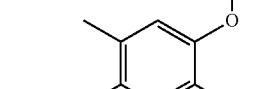

4-methoxy-2,5-
dimethylaniline

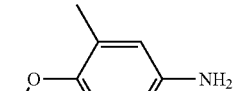

4-ethoxy-3-
methylaniline

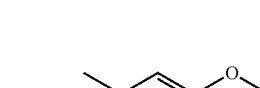

4-ethoxy-2-methylaniline
114766-05-1

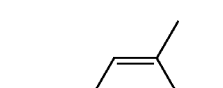

4-methoxy-2,6-
dimethylaniline

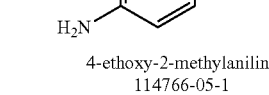

4-amino-2,6-dimethylanisole
39785-37-0

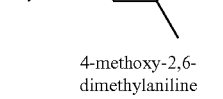

4-methoxy-2,3-dimethylphenylamine
77375-19-0

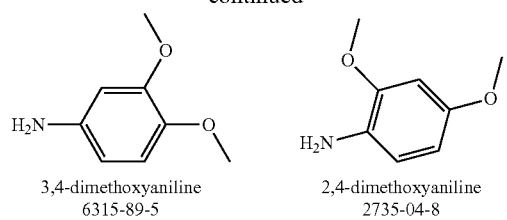

3,4-dimethoxyaniline
6315-89-5

2,4-dimethoxyaniline
2735-04-8

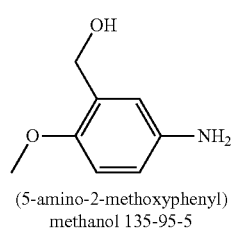
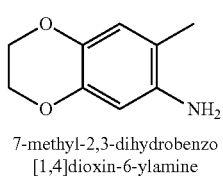

(5-amino-2-methoxyphenyl)
methanol 135-95-5

7-methyl-2,3-dihydrobenzo
[1,4]dioxin-6-ylamine

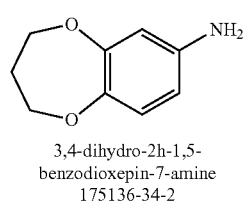
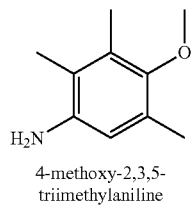

3,4-dihydro-2h-1,5-
benzodioxepin-7-amine
175136-34-2

4-methoxy-2,3,5-
triimethylaniline

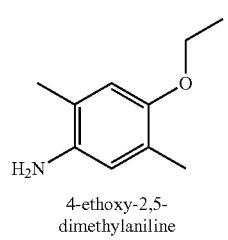
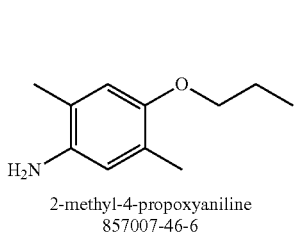

4-ethoxy-2,5-
dimethylaniline 2-methyl-4-propoxyaniline
857007-46-6

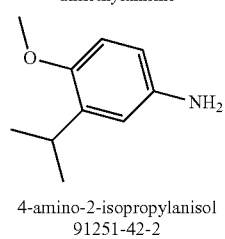
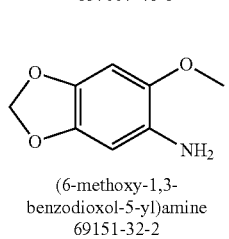

4-amino-2-isopropylanisol
91251-42-2

(6-methoxy-1,3-
benzodioxol-5-yl)amine
69151-32-2

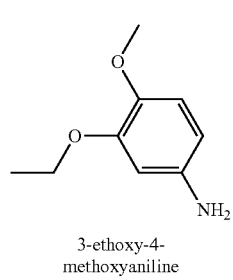
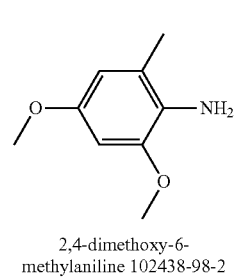

3-ethoxy-4-
methoxyaniline 2,4-dimethoxy-6-
methylaniline 102438-98-2

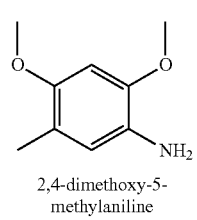
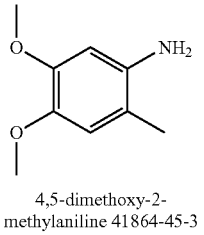

2,4-dimethoxy-5-
methylaniline 4,5-dimethoxy-2-
methylaniline 41864-45-3

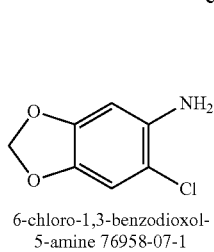
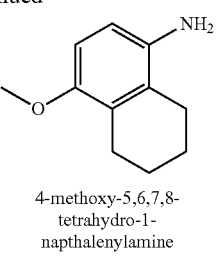

6-chloro-1,3-benzodioxol-
5-amine 76958-07-1

4-methoxy-5,6,7,8-
tetrahydro-1-
napthalenylamine

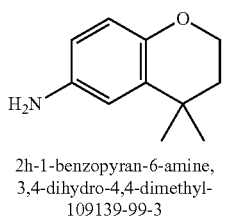
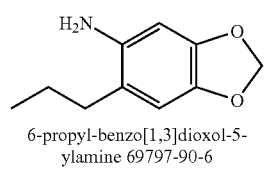

2h-1-benzopyran-6-amine,
3,4-dihydro-4,4-dimethyl-
109139-99-3

6-propyl-benzo[1,3]dioxol-5-
ylamine 69797-90-6

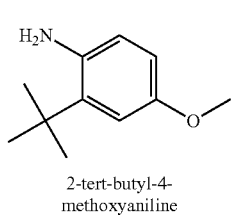
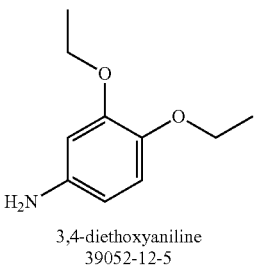

2-tert-butyl-4-
methoxyaniline 3,4-diethoxyaniline
39052-12-5

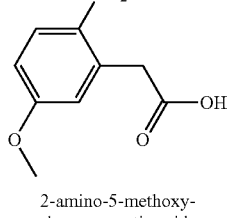
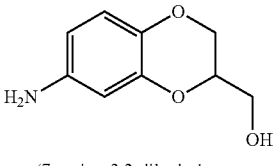

2-amino-5-methoxy-
benzeneacetic acid
38367-42-9

(7-amino-2,3-dihydrobenzo
[1,4]dioxin-2-yl)methanol

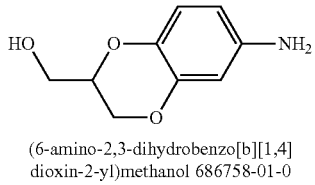

(6-amino-2,3-dihydrobenzo[b][1,4]
dioxin-2-yl)methanol 686758-01-0

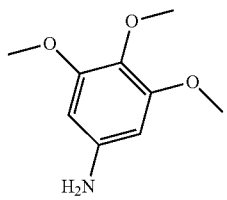
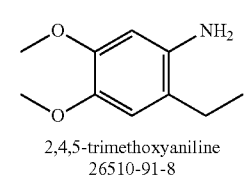

3,4,5-trimethoxyaniline
24313-88-0

2,4,5-trimethoxyaniline
26510-91-8

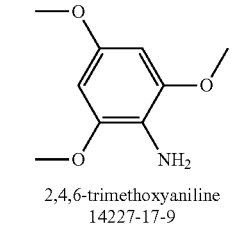

2,3,4-trimethoxyaniline
50625-48-4

2,4,6-trimethoxyaniline
14227-17-9

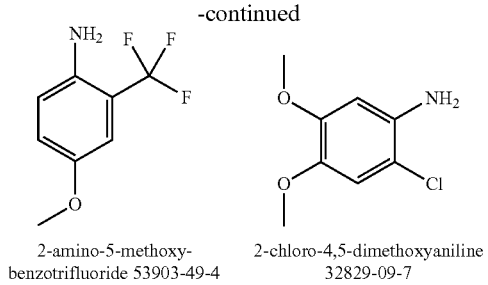

2-amino-5-methoxy-
benzotrifluoride 53903-49-4

2-chloro-4,5-dimethoxyaniline
32829-09-7

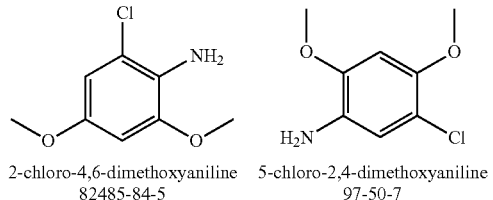

2-chloro-4,6-dimethoxyaniline
82485-84-5

5-chloro-2,4-dimethoxyaniline
97-50-7

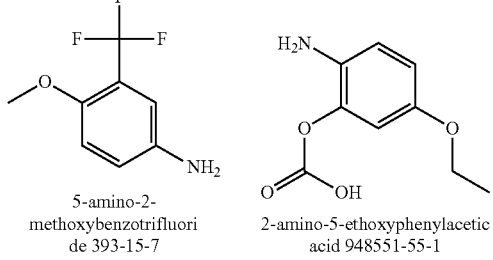

5-amino-2-
methoxybenzotrifluori
de 393-15-7

2-amino-5-ethoxyphenylacetic
acid 948551-55-1

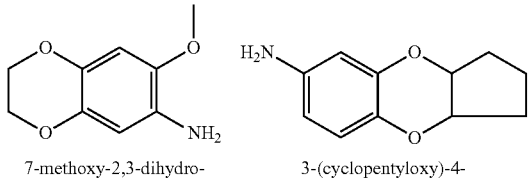

7-methoxy-2,3-dihydro-
1,4-benzodioxin-6-amine 3-(cyclopentyloxy)-4-
methoxyaniline 154464-26-3

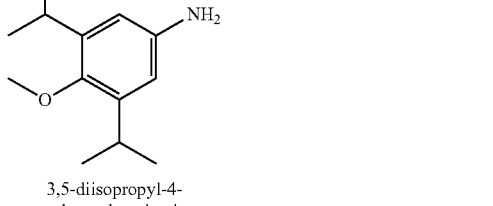

3,5-diisopropyl-4-
methoxyphenylamine

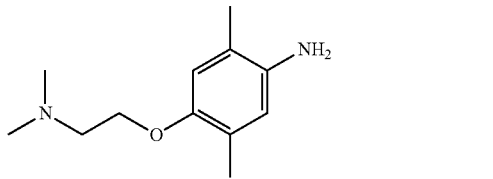

4-[2-(dimethylamino)ethoxy]-
2,5-dimethylaniline

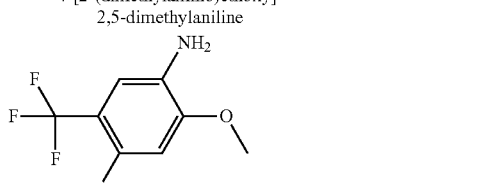

2,4-dimethoxy-5-
(trifluoromethyl)aniline
228401-47-6

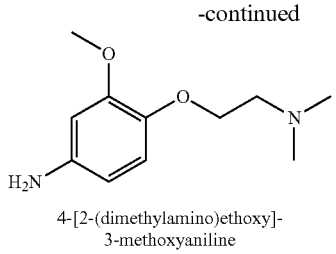

4-[2-(dimethylamino)ethoxy]-
3-methoxyaniline

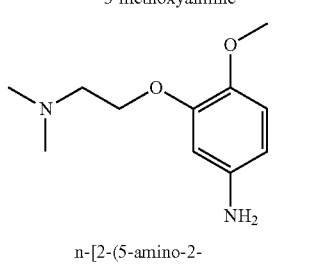

n-[2-(5-amino-2-
methoxyphenoxy)ethyl]-
n,n-dimethylamine 2-bromo-4,5-
dimethoxyaniline
16791-41-6

3-methoxy-4-(2-pyrrolidin-1-yl-
ethoxy)phenylamine 394248-90-9

2-(4-amino-3-
methylphenoxy)ethan-1-ol 2-(5-amino-2-
methoxyphenoxy)thean-1-ol 2-(4-amino-2-
methoxyphenoxy)ethan-1-ol 2-[(7-amino-2,3-dihydro-
1,4-benzodioxin-6-yl)oxy]ethan-1-ol -continued

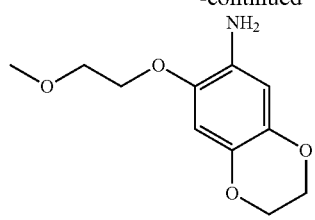

7-(2-methoxyethoxy)-2,3-dihydro-
1,4-benzodioxin-6-amine

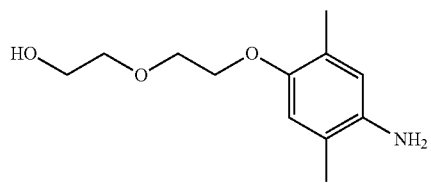

2-[2-(4-amino-2,5-dimethylphenoxy)
ethoxy]ethan-1-ol

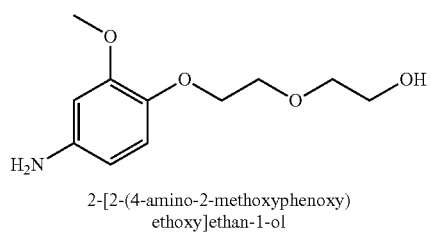

2-[2-(4-amino-2-methoxyphenoxy)
ethoxy]ethan-1-ol

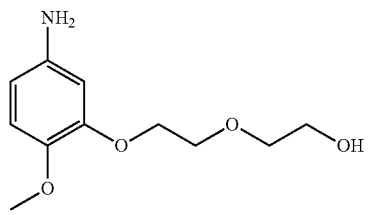

2-[2-(5-amino-2-methoxyphenoxy)
ethoxy]ethan-1-ol

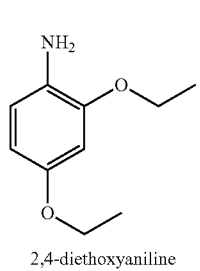

2,4-diethoxyaniline

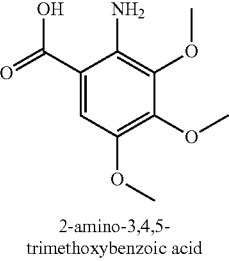

2-amino-3,4,5-
trimethoxybenzoic acid
61948-85-4 Natural

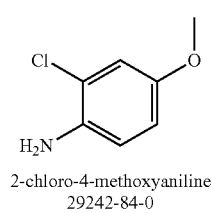

2-chloro-4-methoxyaniline
29242-84-0

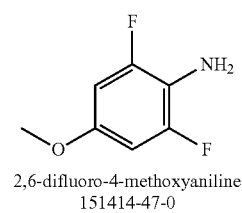

2,6-difluoro-4-methoxyaniline
151414-47-0

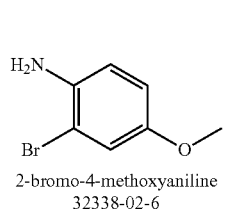

2-bromo-4-methoxyaniline
32338-02-6

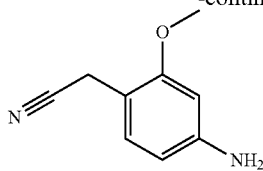

4-amino-2-
methoxyphenylacetonitrile

2-Radical Monoaminobenzene Bases

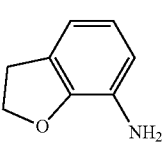

2,3-dihydrobenzo[b]
furan-7-ylamine 13414-56-7

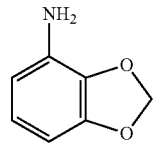

1,3-benzodioxol-4-
amine 1668-84-4

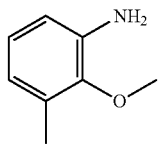

2-methoxy-3-
methylaniline

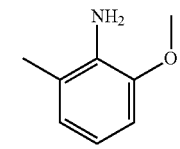

2-methoxy-6-
methylaniline 50868-73-0

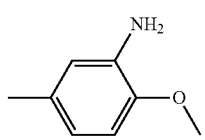

2-methoxy-5-
methylaniline 120-71-8

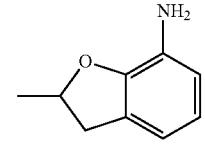

2-methyl-2,3-dihydrobenzo-
furan-7-amine 26210-74-2

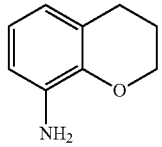

3,4-dihydro-2H-
chromen-8-amine

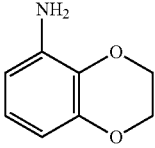

5-amino-1,4-
benzodioxane 16081-45-1

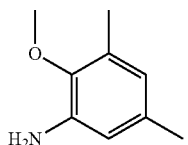

2-methoxy-3,5-
dimethylaniline

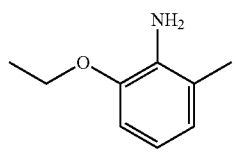

2-ethoxy-6-
methylaniline

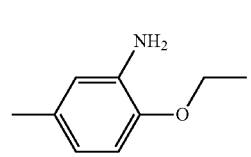

2-ethoxy-5-
methylaniline 6331-70-0

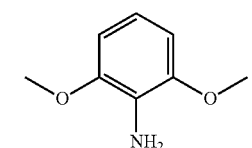

2,6-dimethoxyaniline
2734-70-5

-continued

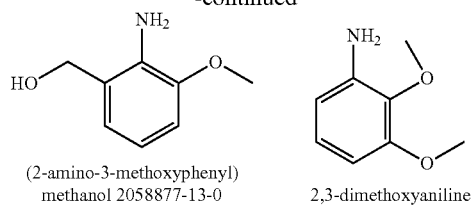

(2-amino-3-methoxyphenyl)
methanol 2058877-13-0

2,3-dimethoxyaniline

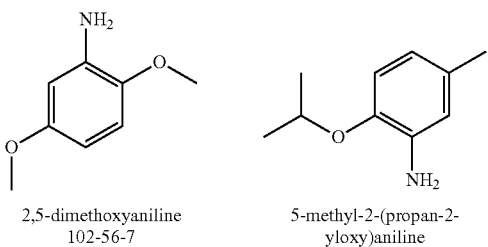

2,5-dimethoxyaniline
102-56-7

5-methyl-2-(propan-2-
yloxy)aniline

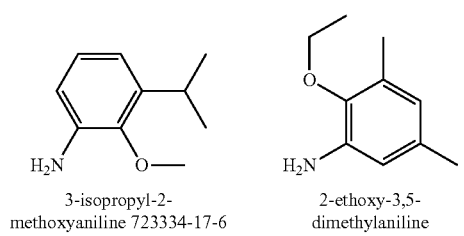

3-isopropyl-2-
methoxyaniline 723334-17-6

2-ethoxy-3,5-
dimethylaniline

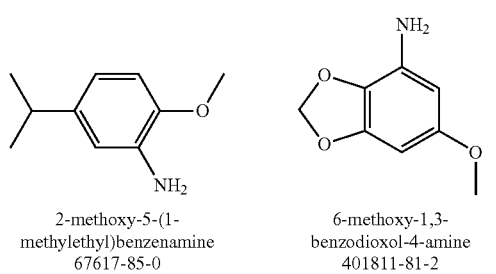

2-methoxy-5-(1-
methylethyl)benzenamine
67617-85-0

6-methoxy-1,3-
benzodioxol-4-amine
401811-81-2

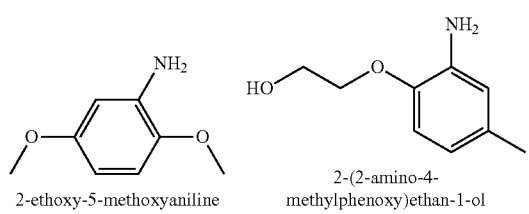

2-ethoxy-5-methoxyaniline 2-(2-amino-4-
methylphenoxy)ethan-1-ol

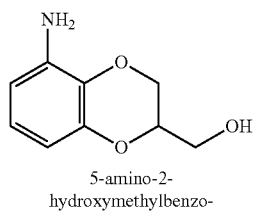

5-amino-2-
hydroxymethylbenzo-
1,4-dioxane 2,6-diethoxyaniline

-continued

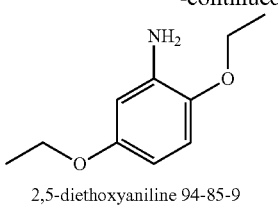

2,5-diethoxyaniline 94-85-9

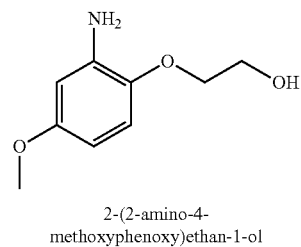

2-(2-amino-4-
methoxyphenoxy)ethan-1-ol

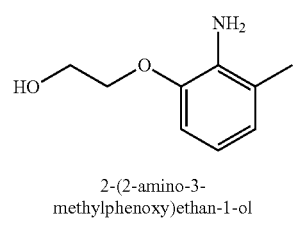

2-(2-amino-3-
methylphenoxy)ethan-1-ol

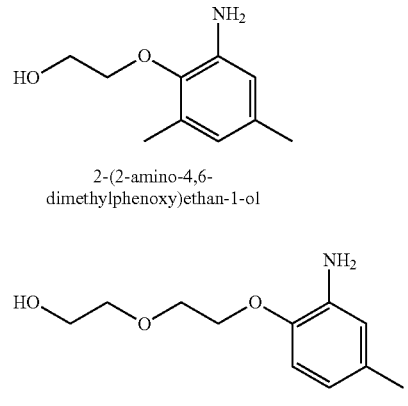

2-(2-amino-4,6-
dimethylphenoxy)ethan-1-ol

2-[2-(2-amino-4-
methylphenoxy)ethoxy]ethan-1-ol

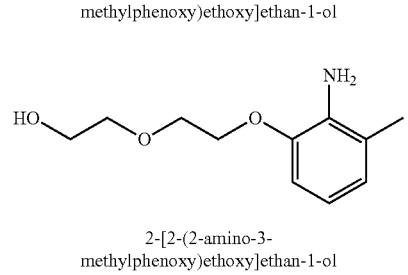

2-[2-(2-amino-3-
methylphenoxy)ethoxy]ethan-1-ol

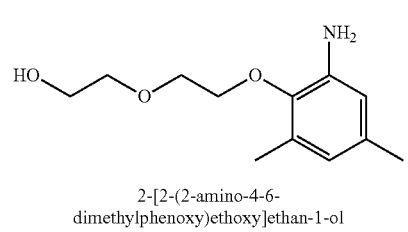

2-[2-(2-amino-4-6-
dimethylphenoxy)ethoxy]ethan-1-ol

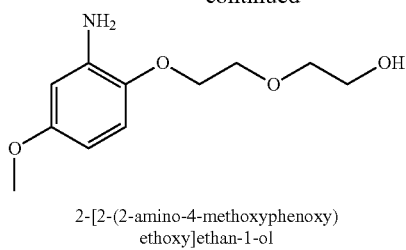

2-[2-(2-amino-4-methoxyphenoxy)
ethoxy]ethan-1-ol

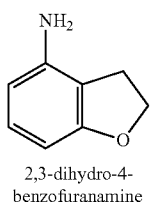

2,3-dihydro-4-
benzofuranamine
61090-37-7

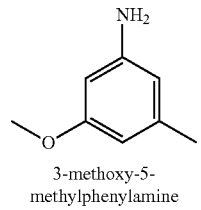

3-methoxy-5-
methylphenylamine
66584-31-4

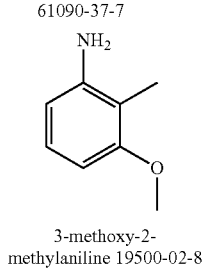

3-methoxy-2-
methylaniline 19500-02-8

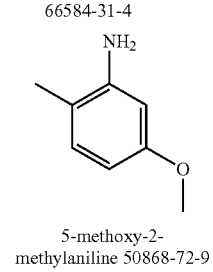

5-methoxy-2-
methylaniline 50868-72-9

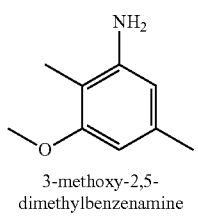

3-methoxy-2,5-
dimethylbenzenamine

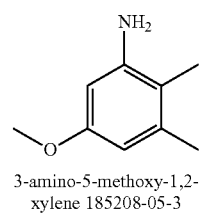

3-amino-5-methoxy-1,2-
xylene 185208-05-3

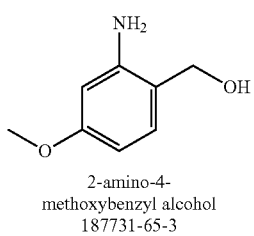

2-amino-4-
methoxybenzyl alcohol
187731-65-3

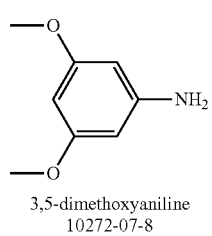

3,5-dimethoxyaniline
10272-07-8

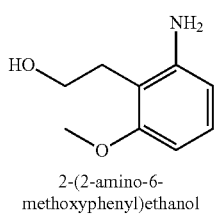

2-(2-amino-6-
methoxyphenyl)ethanol

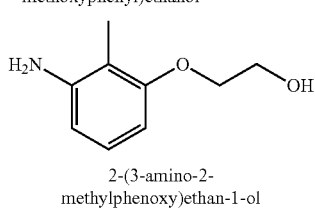

2-(3-amino-2-
methylphenoxy)ethan-1-ol

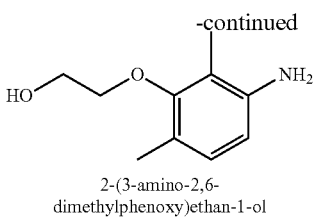

2-(3-amino-2,6-
dimethylphenoxy)ethan-1-ol

According to a particular embodiment, the monoaminobenzene of formula (I) is such that two of the radicals are other than a hydrogen atom, these two radicals being chosen from C1-C4 alkyl and C1-C4 alkoxy radicals with, among these two radicals, at least one alkoxy radical.

Preferably, the compound of formula (I) is chosen from 4-methoxy-2-methylaniline, 3-methoxy-4-methylaniline, 2,5-dimethoxyaniline, 2,6-dimethoxyaniline and 2,4-dimethoxyaniline, salts thereof and solvates thereof.

Preferably, the compounds of formula (I) are present in an amount of between 0.0001% and 10% and preferentially between 0.01% and 5% by weight relative to the total weight of composition (A).

Composition (A) that is useful in the invention comprises an oxidizing agent. Finally, the process is performed with a composition (A) comprising one or more oxidizing agents.

For the purposes of the invention, an oxidizing agent is a chemical oxidizing agent other than atmospheric oxygen.

More particularly, the oxidizing agent(s) are chosen from hydrogen peroxide, urea peroxide, alkali metal bromates or ferricyanides, peroxygenated salts, for instance alkali metal or alkaline-earth metal persulfates, perborates, peracids and precursors thereof, and percarbonates of alkali metals or alkaline-earth metals, and peracids and precursors thereof.

The oxidizing agent is preferably hydrogen peroxide.

This oxidizing agent advantageously consists of hydrogen peroxide, the concentration of which may range more particularly from 0.1% to 50% by weight, even more preferentially from 0.5% to 20% by weight and better still from 1% to 15% by weight relative to composition (A).

The process according to the present invention is performed using a composition (A) comprising at least one compound of formula (I) and additional oxidation dyes other than the compounds of formula (I).

The additional oxidation dyes are generally chosen from the oxidation bases defined below and couplers.

By way of example, the additional oxidation bases are chosen from para-phenylenediamines, bis(phenyl)alkylenediamines, para-aminophenols, ortho-aminophenols and heterocyclic bases, and the addition salts thereof.

According to a preferred embodiment, the composition contains an additional oxidation base chosen from heterocyclic bases, in particular pyridine derivatives, pyrimidine derivatives, pyrazole derivative and mixture thereof, particularly additional oxidation bases of formula (III), their addition salts or solvates:

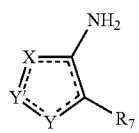

(III)

in which:
X is a —CO— or —CR$_{10}$— group,
Y is a nitrogen atom or a —NR$_8$ group
Y' is a nitrogen atom or a —NR$_9$, group with $R_{10}$ representing a hydrogen atom, a $C_1$-$C_4$ alkyl radical, which is optionally substituted with one or more hydroxyl or amino groups, $R_8$ represents a C1-C4 alkyl radical substituted with one or more hydroxyl or amino groups;

$R_9$ represents a $C_1$-$C_4$ alkyl radical, which is optionally substituted with one or more hydroxyl or amino groups, $R_8$ and $R_9$ on the one hand, and $R_9$ and $R_{10}$ on the other hand, can form with the atoms that bear them a saturated or unsaturated 5 to 7 membered heterocycle, optionally substituted with one or more halogen atom, one or more hydroxy, amino, or $C_1$-$C_4$ alkyl radical, $R_7$ represents an amino group, a $C_1$-$C_4$ alkyl radical group, optionally substituted with one or more hydroxyl or amino groups, a $C_1$-$C_4$ alkoxy group optionally substituted with one or more hydroxyl or amino groups, the ring containing X, Y and Y' comprising at least a double bond.

Oxidation bases of formula (III) or the addition salts may be under the form of solvates, for example hydrates or linear or branched alcohol solvates such as ethanol or isopropanol.

In a first embodiment, the oxidation bases of formula (III) are chosen from compounds of formula (III'), their addition salts or solvates:

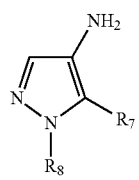

(III')

$R_7$ and $R_8$ having the same meaning as previously defined.

$R_8$ preferably represents a $C_1$-$C_4$ alkyl group substituted with at least one hydroxyl group, particularly a hydroxyethyl group, and $R_7$ represents an amino group.

In this embodiment, 2-(4,5-diamino-1H-pyrazol-1-yl)ethanol or an addition salt is preferred.

In a second embodiment, $R_8$ and $R_9$ on the one hand and $R_9$ and $R_{10}$ on the other hand, form with the atoms that bear them a saturated or unsaturated 5 to 7 membered heterocycle, optionally substituted with one or more halogen atom, one or more hydroxy, amino, or $C_1$-$C_4$ alkyl radical group.

In this second embodiment, the oxidation bases are preferably chosen from:

a) compounds of formula (III''), theirs addition salts and solvates:

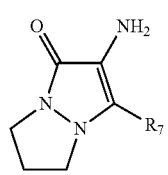

(III'')

$R_7$ having the same meaning as previously defined, and $R_7$ preferably represents an amino group b) compounds of formula (III'''), their addition salts and solvates:

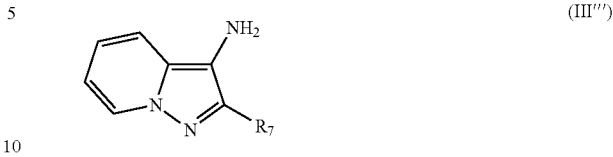

(III''')

$R_7$ having the same meaning as previously defined.

$R_7$ preferably represents a $C_1$-$C_4$ alkoxy group optionally substituted with at least one hydroxy group, particularly a hydroxyethoxy group.

Among the compounds of formula (III''), 2,3-diamino-6,7-dihydro-1H,5H-pyrazolo[1,2-A]pyrazol-1-one or and addition salt is preferred. Among the compounds of formula (III'''), 2-[3-aminopyrazolo[1,5-a]pyridin-2-yl]oxy]ethanol or an addition salt are preferred.

According to another preferred embodiment, the composition contains an additional oxidation base chosen from para phenylene diamine of formula (IV) their addition salts and solvates:

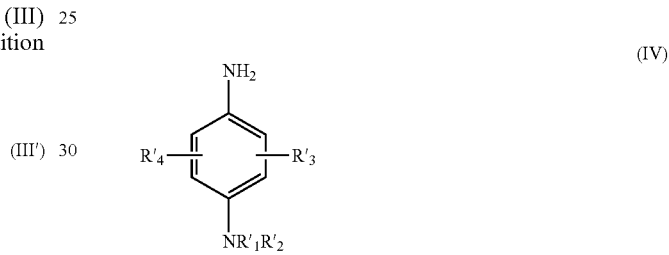

(IV)

in which:

$R'_1$, $R'_2$, $R'_3$, $R'_4$ represent independently of each other a hydrogen atom, a linear or branched C1-C6 and preferably C1-C4 alkyl radical, a linear or branched C1-C6 and preferably C1-C4 hydroxy-alkyl radical, a linear or branched C1-C6 and preferably C1-C4 alcoxy-alkyl group.

$R'_1$ and $R'_2$ preferably represent independently of each other a linear or branched C1-C4 alkyl radical, a linear or branched C1-C4 hydroxy-alkyl radical or a linear or branched C1-C4 alcoxy-alkyl group, preferably a linear or branched C1-C4 hydroxy-alkyl radical.

$R'_1$ and $R'_2$ preferably represent a hydrogen atom.

As example of paraphenylene diamine of formula (IV), mention may be made of para-phenylene diamine, para-toluene diamine, N'N-bis(2-hydroxyethyl)-p-phenylenediamine.

Composition (A) may also comprise one or more couplers. Among these couplers, mention may be made especially of meta-phenylenediamines, meta-aminophenols, meta-diphenols, monophenols, naphthalene-based couplers and heterocyclic couplers, and also the addition salts thereof.

In general, the addition salts of the oxidation bases and couplers that may be used in the context of the invention are especially chosen from addition salts with an acid such as hydrochlorides, hydrobromides, sulfates, citrates, succinates, tartrates, lactates, tosylates, benzenesulfonates, phosphates and acetates.

The additional oxidation base(s) each advantageously represent from 0.0001% to 10% by weight relative to the total weight of the composition, and preferably from 0.005% to 5% by weight relative to the total weight of composition (A).

The content of coupler(s), if they are present, each advantageously represent from 0.0001% to 10% by weight relative to the total weight of the composition, and preferably from 0.005% to 5% by weight relative to the total weight of composition (A).

According to one embodiment of the invention, the composition comprises at least one oxidation base of formula (I) and at least one coupler, and preferably at least 10% of fatty substance. According to a particular embodiment, the fatty substance is liquid.

According to a particular embodiment, composition (A) comprises one or more nonionic, preferably oxyalkylenated, surfactants.

In accordance with a preferred embodiment of the invention, the surfactants are oxyalkylenated nonionic surfactants and are chosen from oxyethylenated $C_8$-$C_{30}$ alcohols, and polyoxyethylenated esters of saturated or unsaturated, linear or branched $C_8$-$C_{30}$ acids and of sorbitol.

Preferably, composition (A) comprises one or more nonionic surfactants.

The surfactant content of composition (A) more particularly represents from 0.1% to 50% by weight and preferably from 0.5% to 30% by weight relative to the weight of the composition under consideration.

Compositions (A) and/or (B) may also contain various adjuvants conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners other than the polymers previously mentioned; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition under consideration.

According to one variant, composition (A) may comprise one or more mineral thickeners preferably chosen from organophilic clays.

The organophilic clay can be chosen from montmorillonite, bentonite, hectorite, attapulgite, sepiolite and mixtures thereof. The clay is preferably a bentonite or a hectorite.

These clays can be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by the company Rheox, Tixogel VP by the company United Catalyst and Claytone 34, Claytone 40 and Claytone XL by the company Southern Clay; stearalkonium bentonites, such as those sold under the names Bentone 27 by the company Rheox, Tixogel LG by the company United Catalyst and Claytone AF and Claytone APA by the company Southern Clay; quaternium-18/benzalkonium bentonites, such as those sold under the names Claytone HT and Claytone PS by the company Southern Clay; quaternium-18 hectorites, such as those sold under the names Bentone Gel DOA, Bentone Gel ECO5, Bentone Gel EUG, Bentone Gel IPP, Bentone Gel ISD, Bentone Gel SS71, Bentone Gel VS8 and Bentone Gel VS38 by the company Rheox, and Simagel M and Simagel SI 345 by the company Biophil.

In another variant, composition (A) comprises at least one organic thickener.

When it is present, the thickener represents from 1% to 30% by weight relative to the weight of the composition.

Advantageously, the composition is in the form of a gel or a cream.

Compositions (A), (A'), (B) or (C) may be anhydrous or aqueous.

More particularly, for the purposes of the invention, the expression "anhydrous cosmetic composition" means a cosmetic composition with a water content of less than 5% by weight, preferably less than 2% by weight and even more preferably less than 1% by weight relative to the weight of the said composition. It should be noted that the water in question is more particularly bound water, such as the water of crystallization in salts, or traces of water absorbed by the raw materials used in the production of the compositions according to the invention.

The term "aqueous composition" is intended to mean a composition comprising more than 5% by weight of water, preferably more than 10% by weight of water and even more advantageously more than 20% by weight of water.

Preferably, composition (A) is an aqueous composition.

Even more preferentially, the water concentration of composition (A) may range from 10% to 90% and better still from 20% to 80% of the total weight of the composition.

Compositions (A), (A'), (B) or (C) may optionally comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The organic solvent(s), if they are present, represent a content usually ranging from 1% to 40% by weight and preferably from 5% to 30% by weight relative to the weight of the composition containing them.

The pH of compositions (A) and (B), if they are aqueous, ranges from 2 to 13. For composition (A), it preferably ranges from 6.5 to 12 and better still from 8 to 12. The pH is adapted by using additional acidifying or basifying agents, such as those mentioned below.

Preferably, compositions (A) and/or (B) comprise one or more alkaline agents. By way of example, mention may be made of mineral amines such as aqueous ammonia or organic amines. Organic amines chosen from alkanolamines such as monoalkanolamines, dialkanolamines or trialkanolamines comprising one to three identical or different $C_1$-$C_4$ hydroxyalkyl radicals, in particular monoethanolamine, are particularly suitable.

As indicated previously, composition (A) may result from the mixing of a composition (A') comprising one or more oxidation dyes as defined previously and a composition (C) comprising one or more oxidizing agents as defined previously. Compositions (A') and (C) are preferably aqueous. They may especially be in the form of direct or inverse emulsions.

They may also result from the mixing of three compositions, the first two being compositions (A') and (B) above and the third composition being a composition (D) comprising at least one fatty substance as defined previously.

This composition (D) may be anhydrous or aqueous. It is preferably anhydrous.

Usually, the pH of the oxidizing composition (C), when it is aqueous, is less than 7.

In a first variant of the invention, composition (A) and composition (B), which composition (A) may result from the extemporaneous mixing of compositions (A'), (C) and optionally (D), are applied successively to wet or dry keratin fibres, with or without intermediate rinsing.

Preferably, according to this second variant, there is no intermediate rinsing.

Preferably, composition (B) is applied before composition (A).

The leave-on time of composition (B) on the keratin fibres may range from 5 to 15 minutes and is preferably 10 minutes.

In particular, composition (B) is applied to the keratin fibres and is left on for 10 minutes at room temperature.

Preferably, composition (B) is sprayed onto the keratin fibres.

In addition, composition (A) may be left in place on the keratin fibres for a time generally of about from 1 minute to 1 hour, preferably from 5 minutes to 40 minutes and preferably for 35 minutes.

The temperature during the process is conventionally between room temperature (between 15 and 25° C.) and 80° C. and preferably between room temperature and 60° C.

According to a preferred embodiment, composition (B) and then composition (A) are applied successively, and without intermediate rinsing, to wet or dry keratin fibres, and the fibres are then dried at a temperature ranging from room temperature to 60° C., preferably at 60° C.

The drying step may last from 5 to 20 minutes, preferably from 5 to 15 minutes, and in particular lasts 10 minutes.

After the treatment, the human keratin fibres are optionally rinsed with water, optionally washed with a shampoo and then rinsed with water, before being dried or left to dry.

After the treatment, the keratin fibres are generally dried under a hood at a temperature ranging from 50 to 80° C.

According to one embodiment, the process for dyeing keratin fibres comprises the use:

(a) of a composition (B) comprising one or more metal catalysts chosen from transition metal salts, in particular organic acid salts of transition metals, and rare-earth metal salts, in particular mineral salts of rare-earth metals, preferably manganese salts, (b) of an anhydrous composition (D) comprising one or more fatty substances chosen from liquid petroleum jelly, $C_6$-$C_{16}$ alkanes, polydecenes, liquid esters of fatty acids and/or of fatty alcohols, and liquid fatty alcohols, or mixtures thereof, preferably in an amount of greater than 35%, (c) of a cosmetic composition (A') comprising one or more oxidation dyes of formula (I), (d) of an oxidizing composition (C) comprising one or more oxidizing agents, and in which composition (B) is applied to the keratin fibres successively and without intermediate rinsing and the keratin fibres are dried, followed by the application to the said fibres of the composition resulting from the extemporaneous mixing of compositions (A), (C) and (D).

According to a second embodiment, compositions (A) and (B) are mixed together, and the mixture made is then applied to wet or dry keratin fibres.

The first variant is preferred.

Finally, the invention relates to a multi-compartment device comprising a first compartment containing a composition (B) comprising one or more metal catalysts as defined previously, a second compartment containing a composition (A') comprising at least one oxidation base of formula (I) as defined previously, and a third compartment containing a composition (C) comprising one or more oxidizing agents as defined previously, preferably at least one fatty substance as defined previously being present in at least one of the compositions (A') or (C), preferentially such that, after mixing together compositions (A') and (C), the fatty substance content is greater than or equal to 10% by weight relative to the total weight of the mixture of compositions (A') and (C). According to a particular embodiment, the device comprises a fourth compartment comprising a composition (D) comprising one or more fatty substances, the said composition (D) being intended to be mixed with compositions (A') and (C), the content of fatty substances of the mixture (A'), (C) and (D) preferably being greater than or equal to 10% and more preferably greater than or equal to 20% by weight relative to the total weight of the mixture of compositions (A'), (C) and (D), composition (A') or (C) possibly containing one or more fatty substances.

The device is suitable for implementing the dyeing process according to the present invention.

The examples that follow serve to illustrate the invention without, however, being limiting in nature.

EXAMPLE 1

1. Preparation of the Composition Based on Metal Salts

Composition (B1) based on metal salts is prepared (the amounts are expressed as weight percentages).

| Composition B1 | |
| --- | --- |
| Laureth-2 | 2 g |
| Decyl glucoside | 2 g |
| Liquid petroleum jelly (mineral oil) | 78.5 g |
| PEG-150/decyl alcohol/SMDI copolymer (Aculyn 44 sold by Röhm & Haas) | 0.5 g |
| Manganese gluconate (CAS No. 6485-39-8) | 0.4 g |
| Water | qs 100 g |

2. Preparation of a Dye Composition A1

The dye composition is prepared at the time of the use by mixing:
 6.7 g of composition D1
 2.7 g of composition A'1 or A'2
 10 g of composition C1
Each of the compositions is described in the following tables, the amounts being expressed as weight percentages, unless otherwise mentioned.
Composition D1

| | |
| --- | --- |
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated (4 OE) sorbitan monolaurate | 11 |
| Glycol distearate | 8 |
| Oxyethylenated (2 OE) lauryl alcohol | 1 |

Composition A'1 containing the monoaminobenzene of formula (I) having a pH adjusted to 7

| | A'1 | A'2 |
| --- | --- | --- |
| Oxidation base of formula (I) | $20 \times 10^{-3}$ mol % | $20 \times 10^{-3}$ mol % |
| Coupler | — | $20 \times 10^{-3}$ mol % |
| Free monoethanolamine | 14.37 g | 14.37 g |
| Sodium metabisulfite | 0.7 g | 0.7 g |

-continued

|  | A'1 | A'2 |
|---|---|---|
| L-Ascorbic acid | 0.25 g | 0.25 g |
| EDTA | 0.287 g | 0.287 g |
| Propylene glycol | 6.2 g | 6.2 g |
| Ethanol | 15 g | 15 g |
| Hexylene glycol | 3 g | 3 g |
| Dipropylene glycol | 3 g | 3 g |
| Benzyl alcohol | 5 g | 5 g |
| Deionized water | qs 100 g | qs 100 g |

Composition C1 (Oxidizing Agent)

| | |
|---|---|
| 50% hydrogen peroxide solution | 12 |
| Liquid petroleum jelly | 20 |
| Cetylstearyl alcohol (30/70 C16/C18) | 8 |
| Oxyethylenated cetylstearyl alcohol (33 OE) | 3 |
| Tetrasodium pyrophosphate decahydrate | 0.03 |
| Sodium hexahydroxystannate | 0.04 |
| Diethylenetriaminepentaacetic acid, pentasodium salt as a 40% aqueous solution | 0.15 |
| Polydimethyldiallylammonium chloride at 40% in water, non-stabilized | 0.5 |
| Poly[(dimethyliminio)-1,3-propanediyl(dimethyliminio)-1,6-hexanediyl dichloride] as an aqueous 60% solution | 0.25 |
| Phosphoric acid | qs pH = 2 |
| Oxyethylenated (4 OE) rapeseed acid amides | 1.3 |
| Vitamin E | 0.1 |
| Glycerol | 0.5 |
| Deionized water | qs 100 |

In composition A'2, the couplers below were used:

| |
|---|
| INCI name |
| Resorcinol |
| meta-Aminophenol |
| Hydroxybenzomorpholine |
| 2-Methyl-5-hydroxyethylaminophenol |
| 2,4-Diaminophenoxyethanol HCl |
| 2-Methylresorcinol |
| 4-Amino-2-hydroxytoluene |
| 6-Hydroxyindole |
| 2-Amino-3-hydroxypyridine |
| 5-Amino-6-chloro-o-cresol |

I. Procedure

Composition (B1) based on metal salts is applied to locks of natural hair containing 90% white hairs (NG). The "composition/lock" bath ratio is respectively 1/1 (g/g). The leave-on time is 10 minutes at room temperature.

The locks of hair are then rinsed and dried manually.

Dye composition A1 is then applied by brush to each of the locks. The "composition/lock" bath ratio is respectively 1/1 (g/g). It is left to stand for 35 minutes at room temperature.

After this leave-on time, the locks of hair are washed with iNOA POST shampoo, rinsed and then dried under a hood at a temperature of 60° C.

II. Results

The colour of the locks was evaluated in the CIE L*a*b* system, using a Minolta Spectrophotometer CM3600D colorimeter. In this L*a*b* system, L* represents the intensity of the colour, a* indicates the green/red colour axis and b* indicates the blue/yellow colour axis. The lower the value of L*, the darker or more intense the colour.

a. Calculation of the Colour Power (DE*)

In the table below, the value of DE* is calculated from the values of L*a*b* according to equation (i) below:

$$DE^* = \sqrt{(L^*-L_o^*)^2 + (a^*-a_o^*)^2 + (b^*-b_o^*)^2} \quad \text{(i)}.$$

The dyeing power is measured from the values L*, a* and b* measured on locks of natural grey hair after dyeing or, alternatively, on locks of permanent-waved grey hair after dyeing, and $L_o^*$, $a_o^*$ and $b_o^*$ represent the values measured on natural undyed locks of grey hair or, respectively, on permanent-waved undyed locks of grey hair.

The greater the value of DE*, the greater the dyeing power.

The results in terms of the build-up are collated in the following table.

| Dyes used | Colour | Hair | L* | a* | b* | DE* |
|---|---|---|---|---|---|---|
| using composition A'1 | | | | | | |
| 4-Methoxy-2-methylaniline | Nacreous | NG | 59.58 | 7.02 | 16.92 | 10.1 |
| 2,5-dimethoxyaniline | Golden | NG | 65.1 | 2.8 | 16.83 | 4.02 |

Good dyeing power is obtained;

| Dyes used | Colour | Hair | L* | a* | b* | DE* build-up |
|---|---|---|---|---|---|---|
| using composition A'2 | | | | | | |
| 4-Methoxy-2-methylaniline + 2,4-diaminophenoxyethanol HCl | Mahogany brown | NG | 29.8 | 7.98 | 9.51 | 35.03 |
| 4-Methoxy-2-methylaniline + 6-hydroxyindole | Coppery brown | NG | 29.17 | 9.71 | 14.21 | 36.07 |
| 4-Methoxy-2-methylaniline + resorcinol | Coppery golden | NG | 57.94 | 7.32 | 17.2 | 10.97 |
| 3-Methoxy-4-methylaniline + 2,4-diaminophenoxyethanol HCl | Dark brown | NG | 29.93 | 6.03 | 9.04 | 34.6 |
| 3-Methoxy-4-methylaniline + 6-hydroxyindole | Mahogany brown | NG | 31.73 | 9.55 | 16.59 | 33.82 |
| 3-Methoxy-4-methylaniline + resorcinol | Brown | NG | 60.49 | 4.81 | 18.24 | 7.68 |
| 2,5-Dimethoxyaniline + 2,4-diaminophenoxyethanol HCl | Dark brown | NG | 34.24 | 6.29 | 10.47 | 32.22 |
| 2,5-Dimethoxyaniline + 6-hydroxyindole | Brown | NG | 32.47 | 7.8 | 15.19 | 34.12 |
| 2,5-Dimethoxyaniline + resorcinol | Golden | NG | 58.39 | 6.05 | 19.21 | 10.6 |

-continued

| Dyes used | Colour | Hair | L* | a* | b* | DE* build-up |
|---|---|---|---|---|---|---|
| 2,5-Dimethoxyaniline + meta-aminophenol | Golden light brown | NG | 47.77 | 6.3 | 18.39 | 19.44 |
| 2,5-Dimethoxyaniline + hydroxybenzomorpholine | Golden light brown | NG | 49.6 | 7.38 | 22.29 | 19.49 |
| 2,5-Dimethoxyaniline + 2-methyl-5-hydroxyethylaminophenol | Dark brown | NG | 61.76 | 4.61 | 17.46 | 6.66 |
| 2,5-Dimethoxyaniline + 2-methylresorcinol | Golden | NG | 59.17 | 3.56 | 17.12 | 7.97 |
| 2,5-Dimethoxyaniline + 4-amino-2-hydroxytoluene | Coppery golden | NG | 58.41 | 5.31 | 18.88 | 10.08 |
| 2,5-Dimethoxyaniline + 2-amino-3-hydroxypyridine | Golden | NG | 56.74 | 6.66 | 20.97 | 12.99 |
| 2,5-Dimethoxyaniline + 5-amino-6-chloro-o-cresol | Golden | NG | 62.87 | 4.08 | 18.43 | 4.06 |
| 2,6-Dimethoxyaniline + 2,4-diaminophenoxyethanol HCl | Brown | NG | 34.47 | 6.31 | 10.93 | 28.74 |
| 2,6-Dimethoxyaniline + 6-hydroxyindole | Coppery brown | NG | 37.30 | 9.56 | 19.48 | 27.85 |
| 2,6-Dimethoxyaniline + resorcinol | Coppery golden | NG | 60.89 | 4.15 | 17.10 | 6.75 |
| 2,4-Dimethoxyaniline + 2,4-diaminophenoxyethanol HCl | Dark brown | NG | 32.39 | 7.61 | 6.96 | 34.68 |
| 2,4-Dimethoxyaniline + 6-hydroxyindole | Dark brown | NG | 31.71 | 9.38 | 12.95 | 34.68 |

When the monoaminobenzene (I) is combined with a coupler, the dyeing power is improved, with a diversified range of tints depending on the combined couplers.

EXAMPLE 2

A composition is prepared according to the composition A'1 with 2,5-dimethoxyaniline as compound of formula (I) and 2-(2,5-diaminophenyl)ethanol sulphate ($20 \times 10^{-3}$ mol %). This composition was mixed as defined above with the composition C1 and D1. The resulting composition was applied on natural locks and permed locks hair according to the process previously disclosed after the application and rinsing of the composition B1 containing manganese salt. The locks were then shampooed, rinsed and dried. The resulting coloration of locks of hair was evaluated in the L*a*b* system.

The selectivity of the coloration is the variation of the color between natural colored hair and permed colored hair. Natural hair is representative of the nature of the hair at the root hair and the permed hair is representative of the nature of the hair at the point.

The selectivity is measured by: ΔE, which is the color variation between a natural colored lock and a permed colored lock, is obtained from the following formula:

$$\Delta E = \sqrt{(L^*-L_o^*)^2+(a^*-a_o^*)^2+(b^*-b_o^*)^2}$$

wherein L* indicates lightness and a* and b* are the chromaticity coordinates of the natural colored locks whereas $L_o^*$ indicates the lightness and $a_o^*$ et $b_o^*$ are the chromaticity of the permed colored locks. The lowest is the value of ΔE, the weakest the selective is the coloration and the best is the color of the hair.

The measured selectivity is reported in the following table:

| | Color | L* | a* | b* | dE* | Selectivity |
|---|---|---|---|---|---|---|
| Natural hair | Brown | 31.2 | 2.5 | 9.9 | 30.8 | 5.9 |
| Permed hair | | 25.5 | 3.1 | 8.1 | 38.6 | |

EXAMPLE 3

The following dyeing compositions were prepared according to the above mentioned composition comprising as base and coupler the one disclosed in the table below.

| | | Color | L* | a* | b* | dE* | % DE after 10 shampoos ** |
|---|---|---|---|---|---|---|---|
| 2,5-dimethoxyaniline | | | | | | | |
| With IA 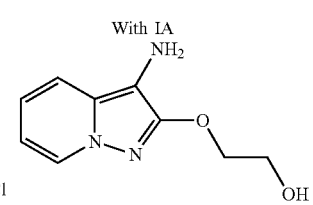 HCl | natural permed | Violet/Black | 20.0 19.1 | 5.3 2.8 | −7.5 −5.0 | 50.7 48.1 | 15.3 0.5 |
| With IB 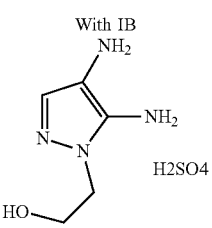 H2SO4 | natural permed | violet | 20.7 18.5 | 7.1 3.5 | −8.4 −3.7 | 50.5 48.2 | 3.2 3.1 |
| With IC 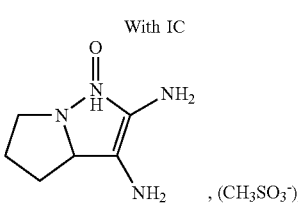 , (CH3SO3⁻)2 | natural permed | rouge | 45.15 40.85 | 27.4 34.9 | 1.3 1.4 | 36.3 43.1 | 18.9 10.7 |
| 2,4-dimethoxyaniline | | | | | | | |
| With IA | natural permed | Brown | 32.0 25.8 | 5.3 4.8 | 2.5 1.24 | 35.6 39.8 | 6.9 4.5 |
| With IB | BN BP | red | 32.1 38.4 | 18.1 15.8 | 9.2 8.8 | 37.3 38.7 | 17.5 10.23 |
| 2-amino-5-chlorophenol | | | | | | | |
| with IA | natural permed | brown | 31.9 37.3 | 3.5 4.0 | 1.4 2.9 | 36.3 38.7 | 14.5 9.6 |
| with IB | natural Permed | red | 30.0 26.8 | 18.5 18.8 | 7.1 6.9 | 40.5 42.2 | 5.9 1.4 |

**% DE after 10 shampoos: (DE after 10 shampoo − DE at the time of dyeing/DE at the time of the dyeing) × 100.

With these compositions, the resulting coloration is intense and with a good shampoo fastness.

The invention claimed is:

1. A process for dyeing keratin fibers, the process comprising:
   applying to the keratin fibers a composition comprising at least one metal catalyst comprising a metal in oxidation state II, and a composition (A) comprising:
   at least one oxidizing agent,
   at least one fatty substance chosen from liquid petroleum jelly, $C_6$-$C_{16}$ alkanes, or polydecenes, present in an amount of at least about 25% by weight, relative to the total weight of composition (A),
   at least one coupler, and
   at least one oxidation base chosen from monoaminobenzenes of formula (I), or an addition salt or solvate thereof:

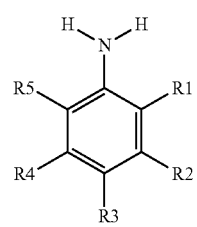

(I)

wherein the radicals R1 to R5, independently of each other, are chosen from:
   hydrogen atoms;
   halogen atoms, F, Cl, or Br;
   linear or branched C1-C6 or C1-C4 alkyl radicals, optionally substituted;
   linear or branched C1-C6 or C1-C4 alkoxy radicals, optionally substituted; or
   carboxylic (—COOH) or sulfonic (—SO3H) radicals;
   wherein two of the adjacent radicals R1 to R5 may form, with the carbon atoms that bear them, a saturated or unsaturated, 5- to 7-membered ring, optionally comprising from 1 to 2 heteroatoms, the ring being optionally fused with a saturated or unsaturated 5- to 6-membered ring;

and with the proviso that at least one of the radicals R1 to R5 represents an optionally substituted alkoxy radical.

2. The process of claim 1, wherein the at least one metal catalyst is chosen from metal salts, metal oxides, metal complexes, transition metal salts, rare-earth metal salts, mineral salts chosen from halides, hydrated halides, anhydrous halides, carbonates, sulfates, or phosphates or mixtures thereof.

3. The process of claim 1, wherein the at least one metal catalyst is chosen from metal salts bearing a metal in oxidation state II and two (poly)hydroxy acid-based ligands.

4. The process of claim 3, wherein the metal salts are chosen from metal salts of formula (II), or hydrates thereof, solvates thereof, or enantiomers thereof:

R—C(O)—O-M-O—C(O)—R'    (II)

wherein:

M is chosen from a metal (II) or metal$^{2+}$ in oxidation state 2 or manganese(II); and R and R', which may be identical or different, represent a (C1-C6)(poly)hydroxyalkyl group.

5. The process of claim 2, wherein the metal salts are organic acid salts chosen from citrates, lactates, glycolates, gluconates, acetates, propionates, fumarates, oxalates, or tartrates.

6. The process of claim 1, wherein the at least one metal catalyst is chosen from organic acid salts of transition metals, organic acid salts of manganese, mineral salts of rare-earth metals, or mineral salts of cerium.

7. The process of claim 1, wherein the composition (A) comprises at least one fatty substance in an amount ranging from about 25% to about 70%, by weight relative to the total weight of composition (A).

8. The process of claim 1, wherein the at least one fatty substance is present in an amount ranging from about 25% to about 60% by weight, relative to the total weight of composition (A).

9. The process of claim 1, wherein the cosmetic composition (A) further comprises at least one surfactant.

10. The process of claim 1, wherein the oxidation base of formula (I) is chosen from the following compounds, salts thereof, or solvates thereof:

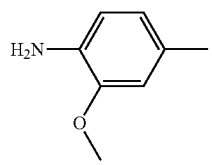

2-methoxy-4-methylaniline 39538-68-6

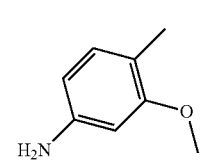

3-methoxy-4-methylaniline 16452-01-0

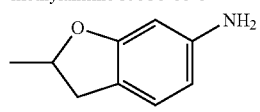

2-methyl-2,3-dihydrobenzofuran-6-amine 129014-10-4

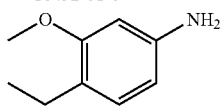

4-ethyl-3-methoxybenzenamine 947691-59-0

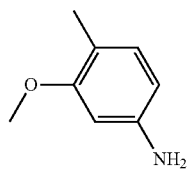

3-ethoxy-4-methylaniline

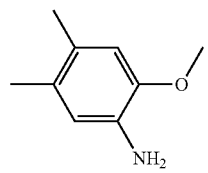

2-methoxy-4,5-dimethylaniline

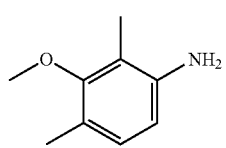

3-methoxy-2,4-dimethylaniline

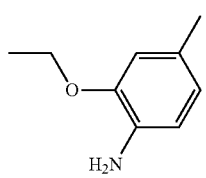

2-ethoxy-4-methylaniline 23385-44-6

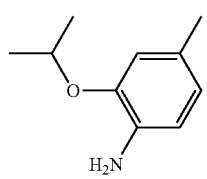

4-methyl-2-(propan-2-yloxy)aniline

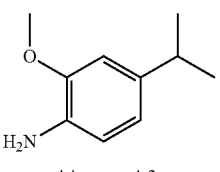

4-isopropyl-2-methoxyphenylamine 1201943-63-6

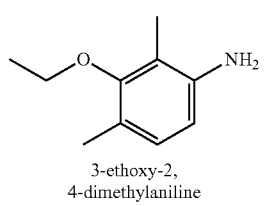

3-ethoxy-2,4-dimethylaniline

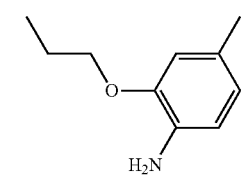

4-methyl-2-propoxyaniline 640767-75-5

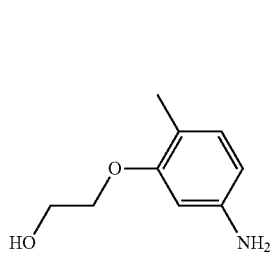

2-(5-amino-2-methylphenoxy)ethan-1-ol

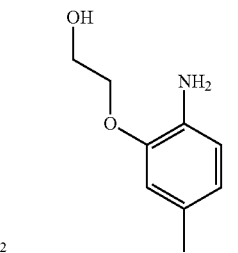

2-(2-amino-5-methylphenoxy)ethan-1-ol

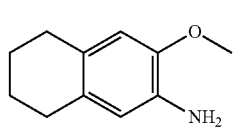

3-methoxy-5,6,7,8-tetrahydronaphthalen-2-ylamine 6240-83-1

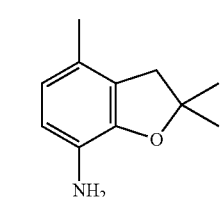

2,2,7-trimethyl-3-oxaindane-4-ylamine

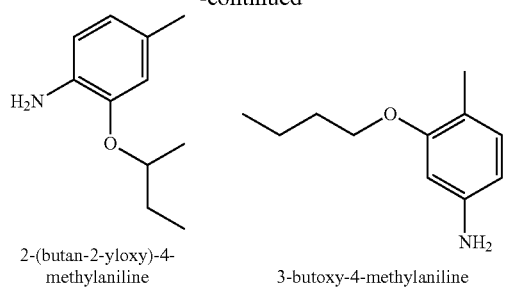

2-(butan-2-yloxy)-4-methylaniline 3-butoxy-4-methylaniline

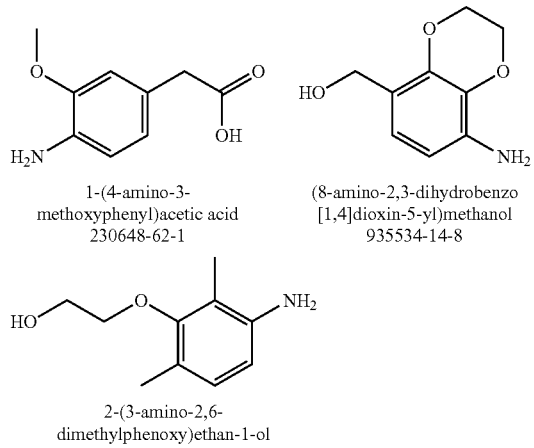

1-(4-amino-3-methoxyphenyl)acetic acid 230648-62-1

(8-amino-2,3-dihydrobenzo[1,4]dioxin-5-yl)methanol 935534-14-8

2-(3-amino-2,6-dimethylphenoxy)ethan-1-ol

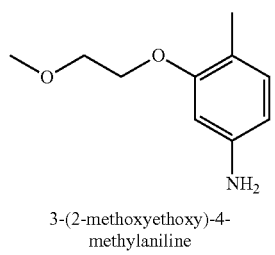

3-(2-methoxyethoxy)-4-methylaniline

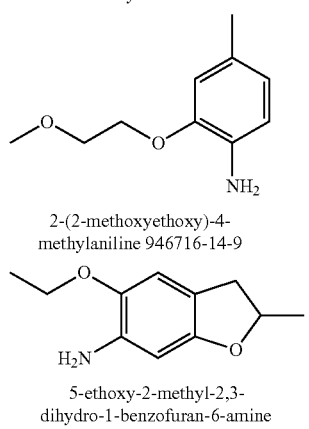

2-(2-methoxyethoxy)-4-methylaniline 946716-14-9

5-ethoxy-2-methyl-2,3-dihydro-1-benzofuran-6-amine

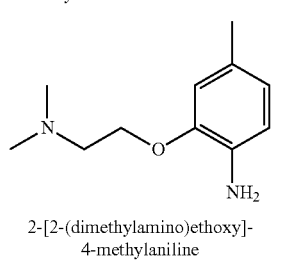

2-[2-(dimethylamino)ethoxy]-4-methylaniline

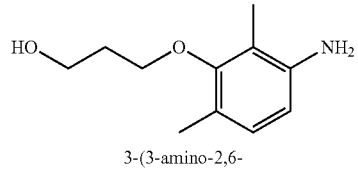

3-(3-amino-2,6-dimethylphenoxy)propan-1-ol

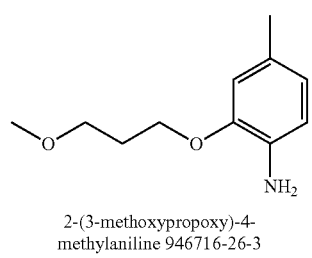

2-(3-methoxypropoxy)-4-methylaniline 946716-26-3

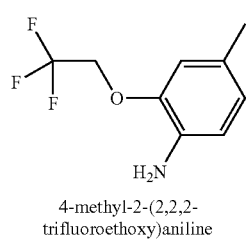

4-methyl-2-(2,2,2-trifluoroethoxy)aniline

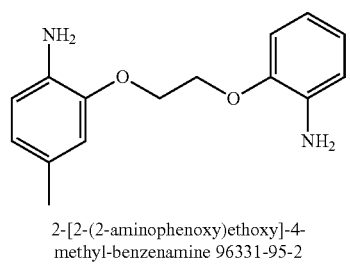

2-[2-(2-aminophenoxy)ethoxy]-4-methyl-benzenamine 96331-95-2

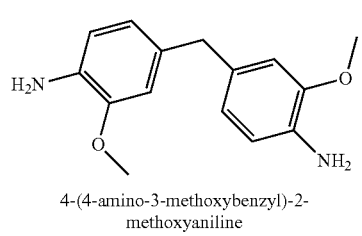

4-(4-amino-3-methoxybenzyl)-2-methoxyaniline

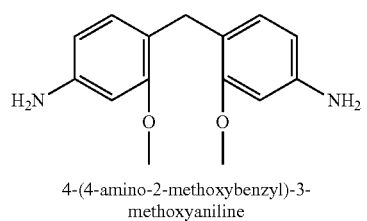

4-(4-amino-2-methoxybenzyl)-3-methoxyaniline

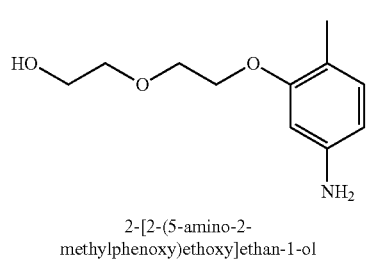

2-[2-(5-amino-2-methylphenoxy)ethoxy]ethan-1-ol 1) para-Aminobenzene oxidation bases:

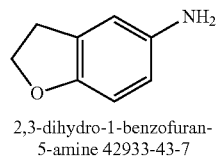
2,3-dihydro-1-benzofuran-5-amine 42933-43-7

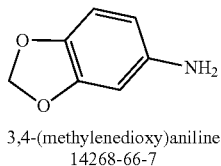
3,4-(methylenedioxy)aniline 14268-66-7

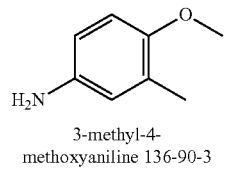
3-methyl-4-methoxyaniline 136-90-3

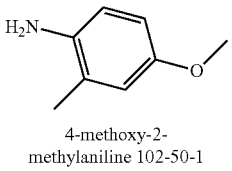
4-methoxy-2-methylaniline 102-50-1

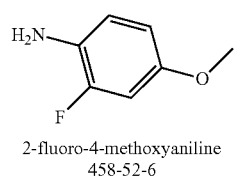
2-fluoro-4-methoxyaniline 458-52-6

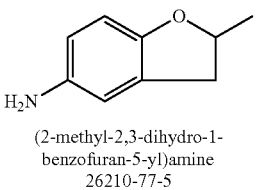
(2-methyl-2,3-dihydro-1-benzofuran-5-yl)amine 26210-77-5

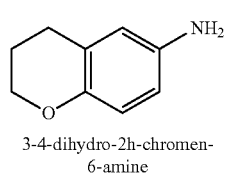
3-4-dihydro-2h-chromen-6-amine

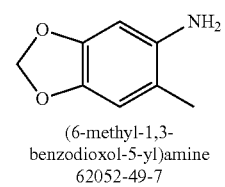
(6-methyl-1,3-benzodioxol-5-yl)amine 62052-49-7

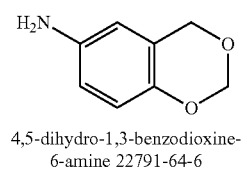
4,5-dihydro-1,3-benzodioxine-6-amine 22791-64-6

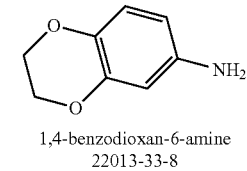
1,4-benzodioxan-6-amine 22013-33-8

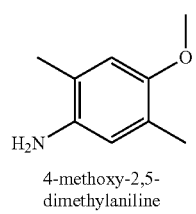
4-methoxy-2,5-dimethylaniline

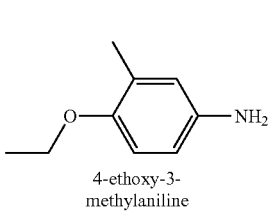
4-ethoxy-3-methylaniline

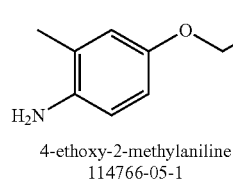
4-ethoxy-2-methylaniline 114766-05-1

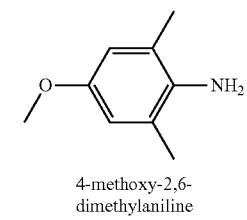
4-methoxy-2,6-dimethylaniline

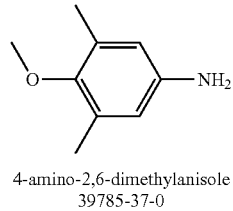
4-amino-2,6-dimethylanisole 39785-37-0

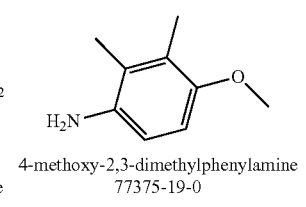
4-methoxy-2,3-dimethylphenylamine 77375-19-0

-continued

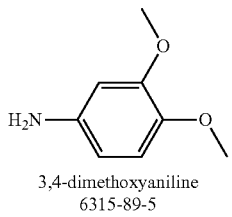
3,4-dimethoxyaniline 6315-89-5

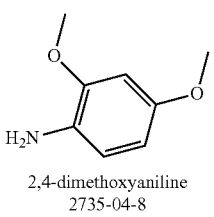
2,4-dimethoxyaniline 2735-04-8

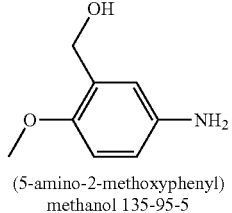
(5-amino-2-methoxyphenyl)methanol 135-95-5

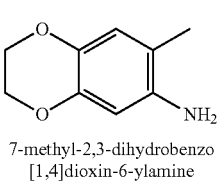
7-methyl-2,3-dihydrobenzo[1,4]dioxin-6-ylamine

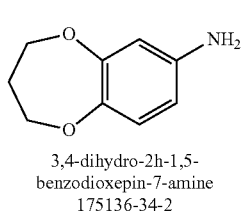
3,4-dihydro-2h-1,5-benzodioxepin-7-amine 175136-34-2

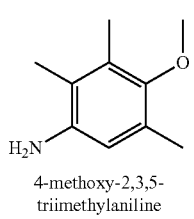
4-methoxy-2,3,5-triimethylaniline

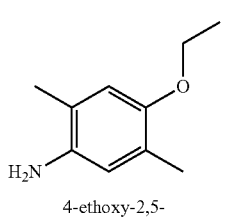
4-ethoxy-2,5-dimethylaniline

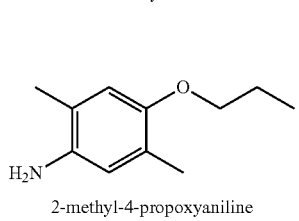
2-methyl-4-propoxyaniline 857007-46-6

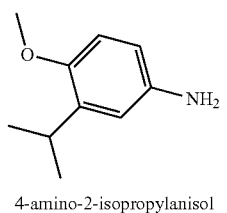
4-amino-2-isopropylanisol 91251-42-2

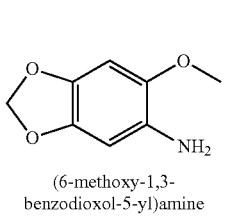
(6-methoxy-1,3-benzodioxol-5-yl)amine 69151-32-2

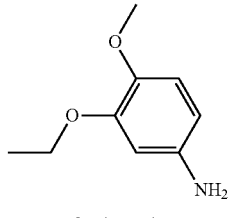
3-ethoxy-4-methoxyaniline

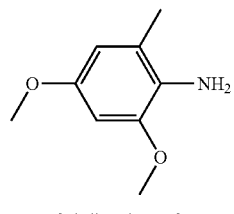
2,4-dimethoxy-6-methylaniline 102438-98-2

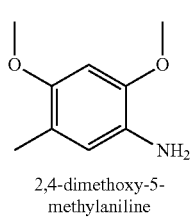
2,4-dimethoxy-5-methylaniline

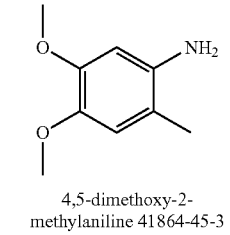
4,5-dimethoxy-2-methylaniline 41864-45-3

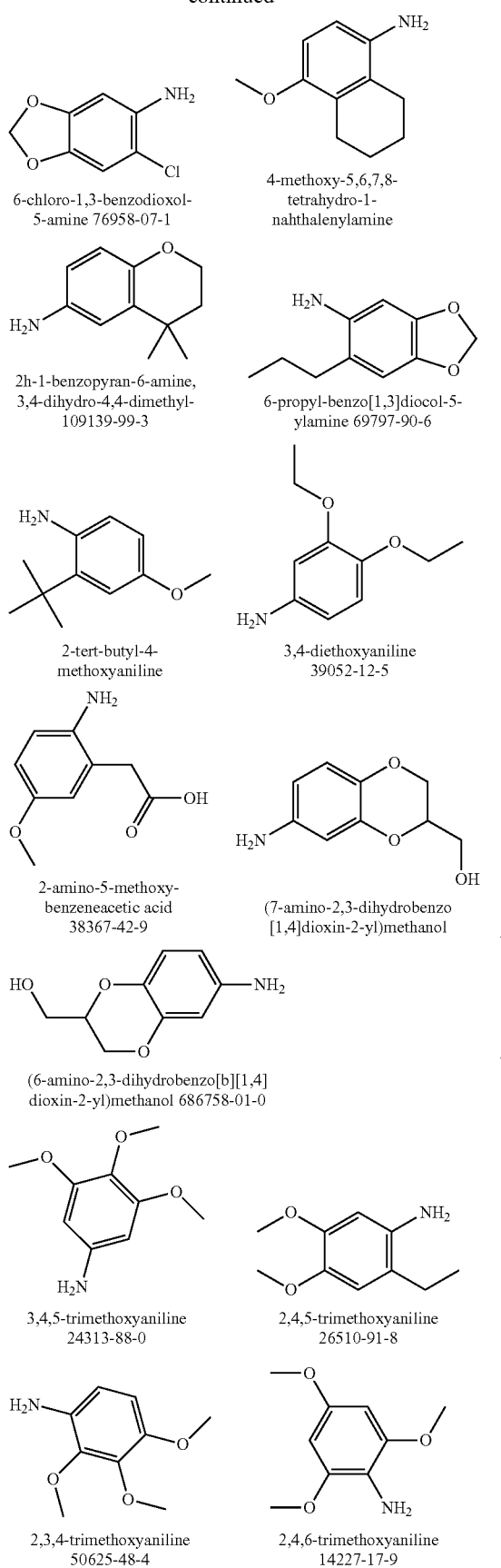
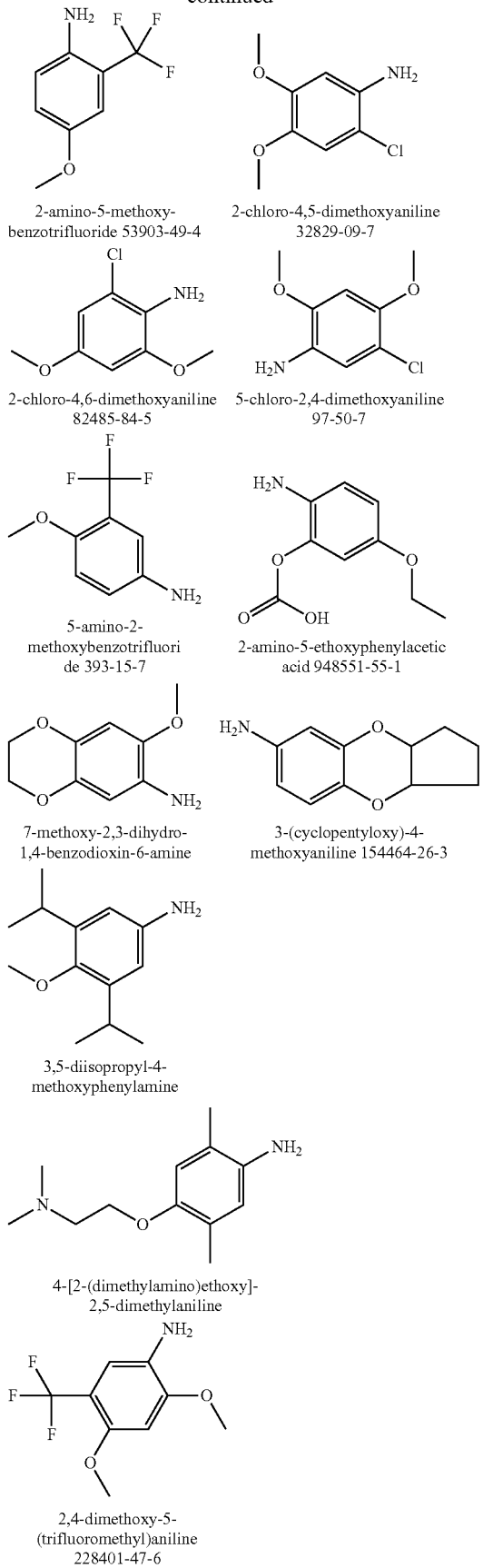

-continued

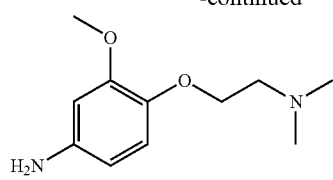

4-[2-(dimethylamino)ethoxy]-
3-methoxyaniline

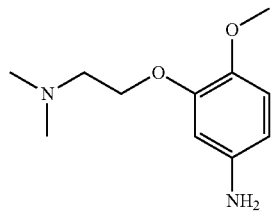

n-[2-(5-amino-2-
methoxyphenoxy)ethyl]-
n,n-dimethylamine 2-bromo-4,5-
dimethoxyaniline
16791-41-6

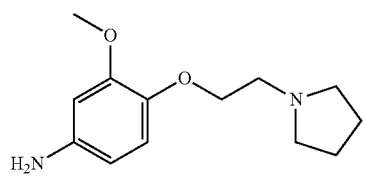

3-methoxy-4-(2-pyrrolidin-1-yl-
ethoxy)phenylamine 394248-90-9

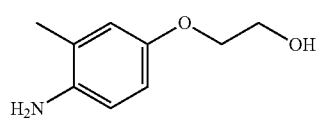

2-(4-amino-3-
methylphenoxy)ethan-1-ol

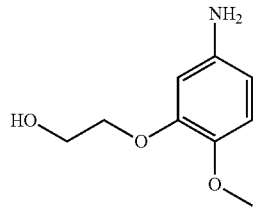

2-(5-amino-2-
methoxyphenoxy)thean-1-ol

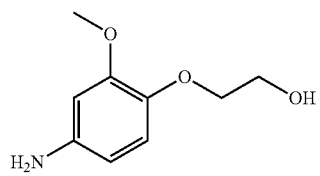

2-(4-amino-2-
methoxyphenoxy)ethan-1-ol

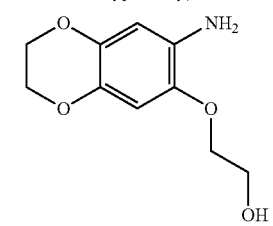

2-[(7-amino-2,3-dihydro-
1,4-benzodioxin-6-yl)oxy]ethan-1-ol

-continued

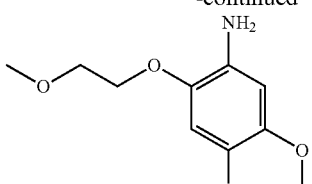

7-(2-methoxyethoxy)-2,3-dihydro-
1,4-benzodioxin-6-amine

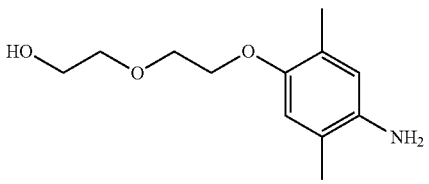

2-[2-(4-amino-2,5-dimethylphenoxy)
ethoxy]ethan-1-ol

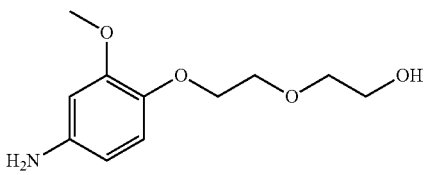

2-[2-(4-amino-2-methoxyphenoxy)
ethoxy]ethan-1-ol

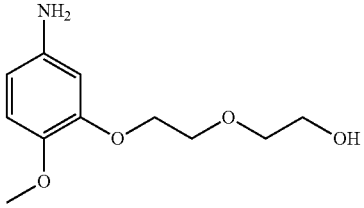

2-[2-(5-amino-2-methoxyphenoxy)
ethoxy]ethan-1-ol

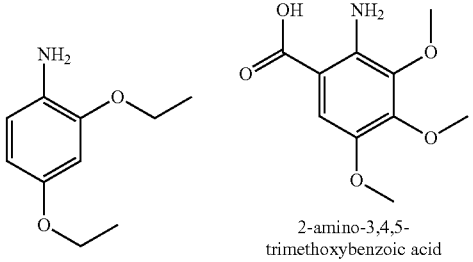

2,4-diethoxyaniline 2-amino-3,4,5-
trimethoxybenzoic acid
61948-85-4 Natural

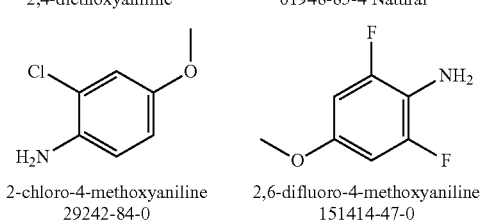

2-chloro-4-methoxyaniline
29242-84-0

2,6-difluoro-4-methoxyaniline
151414-47-0

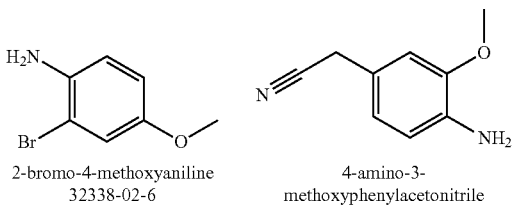

2-bromo-4-methoxyaniline
32338-02-6

4-amino-3-
methoxyphenylacetonitrile

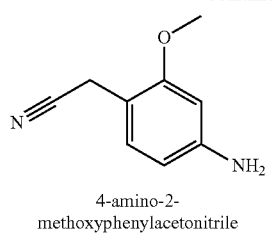

4-amino-2-methoxyphenylacetonitrile

2) Radical monoaminobenzene bases

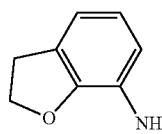

2,3-dihydrobenzo[b]furan-7-ylamine 13414-56-7

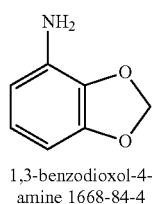

1,3-benzodioxol-4-amine 1668-84-4

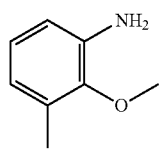

2-methoxy-3-methylaniline

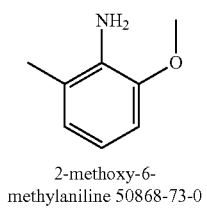

2-methoxy-6-methylaniline 50868-73-0

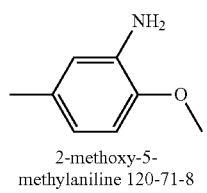

2-methoxy-5-methylaniline 120-71-8

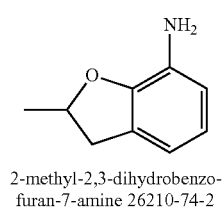

2-methyl-2,3-dihydrobenzofuran-7-amine 26210-74-2

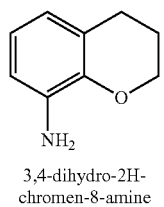

3,4-dihydro-2H-chromen-8-amine

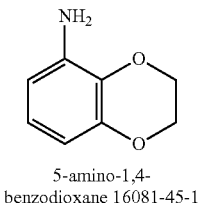

5-amino-1,4-benzodioxane 16081-45-1

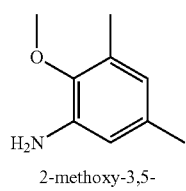

2-methoxy-3,5-dimethylaniline

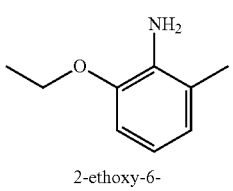

2-ethoxy-6-methylaniline

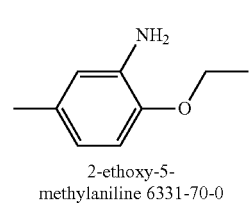

2-ethoxy-5-methylaniline 6331-70-0

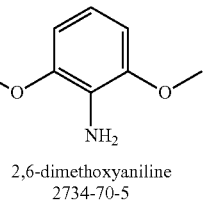

2,6-dimethoxyaniline 2734-70-5

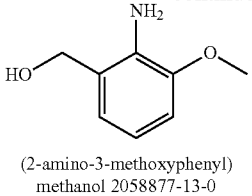

(2-amino-3-methoxyphenyl)methanol 2058877-13-0

2,3-dimethoxyaniline

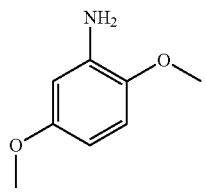

2,5-dimethoxyaniline 102-56-7

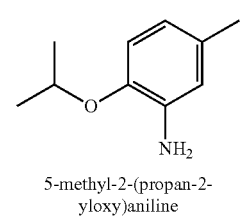

5-methyl-2-(propan-2-yloxy)aniline

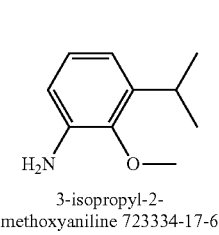

3-isopropyl-2-methoxyaniline 723334-17-6

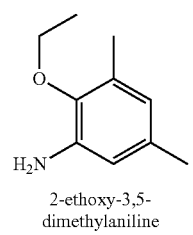

2-ethoxy-3,5-dimethylaniline

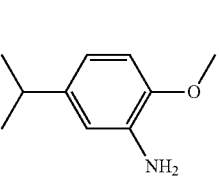

2-methoxy-5-(1-methylethyl)benzenamine 67617-85-0

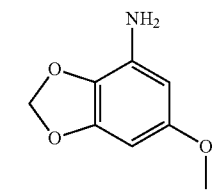

6-methoxy-1,3-benzodioxol-4-amine 401811-81-2

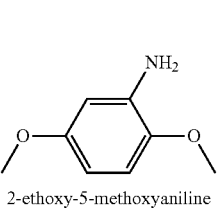

2-ethoxy-5-methoxyaniline

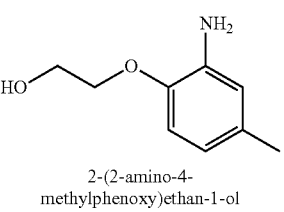

2-(2-amino-4-methylphenoxy)ethan-1-ol

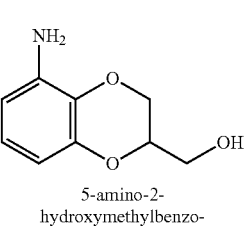

5-amino-2-hydroxymethylbenzo-1,4-dioxane

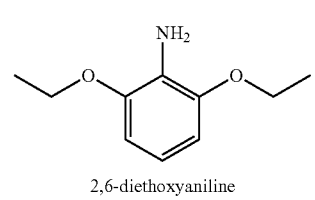

2,6-diethoxyaniline

-continued

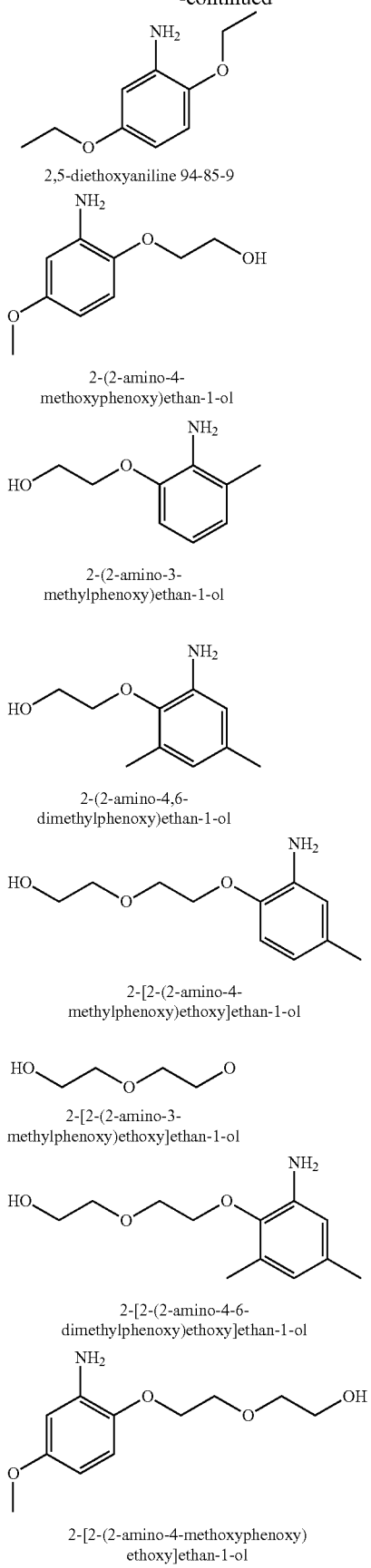

2,5-diethoxyaniline 94-85-9

2-(2-amino-4-methoxyphenoxy)ethan-1-ol 2-(2-amino-3-methylphenoxy)ethan-1-ol 2-(2-amino-4,6-dimethylphenoxy)ethan-1-ol 2-[2-(2-amino-4-methylphenoxy)ethoxy]ethan-1-ol 2-[2-(2-amino-3-methylphenoxy)ethoxy]ethan-1-ol 2-[2-(2-amino-4-6-dimethylphenoxy)ethoxy]ethan-1-ol 2-[2-(2-amino-4-methoxyphenoxy)ethoxy]ethan-1-ol -continued

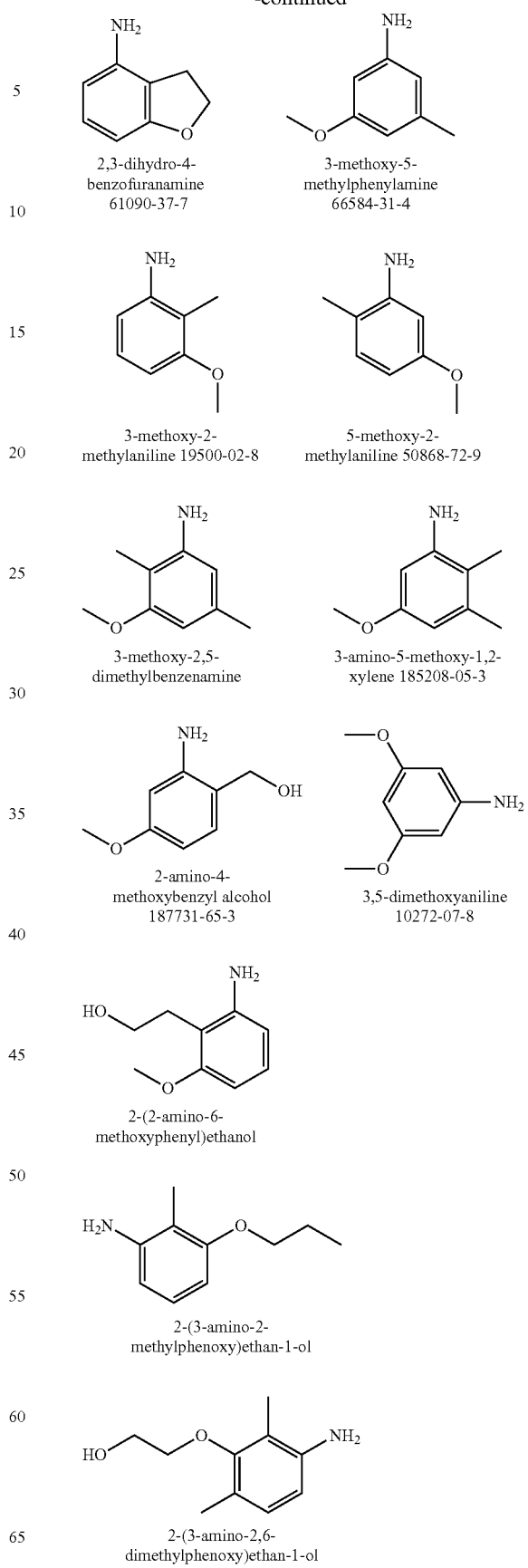

2,3-dihydro-4-benzofuranamine 61090-37-7

3-methoxy-5-methylphenylamine 66584-31-4

3-methoxy-2-methylaniline 19500-02-8

5-methoxy-2-methylaniline 50868-72-9

3-methoxy-2,5-dimethylbenzenamine 3-amino-5-methoxy-1,2-xylene 185208-05-3

2-amino-4-methoxybenzyl alcohol 187731-65-3

3,5-dimethoxyaniline 10272-07-8

2-(2-amino-6-methoxyphenyl)ethanol 2-(3-amino-2-methylphenoxy)ethan-1-ol 2-(3-amino-2,6-dimethylphenoxy)ethan-1-ol 11. The process of claim 1, wherein in the oxidation base of formula (I), at least one of the radicals R1 to R5 is an optionally substituted alkoxy radical, and at least one other of the radicals R1 to R5 is an alkoxy or alkyl radical or forms, with an adjacent radical and the carbon atoms to which they are attached, a ring, and the other radicals are hydrogen atoms.

12. The process of claim 1, wherein the oxidation base of formula (I) is chosen from 4-methoxy-2-methylaniline, 3-methoxy-4-methylaniline, 2,5-dimethoxyaniline, 2,6-dimethoxyaniline, or 2,4-dimethoxyaniline, or salts or solvates thereof.

13. The process of claim 1, wherein the composition comprises an additional oxidation base chosen from heterocyclic oxidation bases chosen from pyrazole or pyrazolinone oxidation bases.

14. The process of claim 1, wherein the oxidizing agent is hydrogen peroxide.

15. The process of claim 1,
wherein a composition (B) comprising the said at least one metal catalyst and composition (A) are mixed together to form a mixture prior to application to the keratin fibers, and
wherein the mixture is applied to wet or dry keratin fibers.

16. The process of claim 1, wherein a composition (B) comprising the said at least one metal catalyst and composition (A) are successively applied to the keratin fibers, with or without intermediate rinsing.

17. The process of claim 1, wherein composition (A) results from the mixing of two or three compositions including at least one composition (A') comprising at least one oxidation base of formula (I) and a composition (C) comprising the at least one oxidizing agent, and optionally a composition (D) comprising the at least one fatty substance.

18. A dye composition comprising:
at least one oxidation base chosen from monoaminobenzenes of formula (I) or an addition salt or solvate thereof:

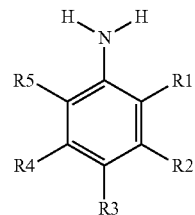

wherein the radicals R1 to R5, independently of each other, are chosen from:
hydrogen atoms;
halogen atoms, F, Cl, or Br;
linear or branched C1-C6 or C1-C4 alkyl radicals, optionally substituted;
linear or branched C1-C6 or C1-C4 alkoxy radicals, optionally substituted;
or
carboxylic (—COOH) or sulfonic (—SO3H) radicals;
wherein two of the adjacent radicals R1 to R5 may form, with the carbon atoms that bear them, a saturated or unsaturated, 5- to 7-membered ring, optionally comprising from 1 to 2 heteroatoms, the ring being optionally fused with a saturated or unsaturated 5- to 6-membered ring; and with the proviso that at least one of the radicals R1 to R5 represents an optionally substituted alkoxy radical,
at least one fatty substance chosen from liquid petroleum jelly, $C_6$-$C_{16}$ alkanes, or polydecenes in an amount of at least about 25%, by weight relative to the total weight of the composition;
at least one coupler; and
an oxidizing agent.

* * * * *

UNITED STATES PATENT AND TRADEMARK OFFICE
CERTIFICATE OF CORRECTION

PATENT NO. : 10,251,827 B2
APPLICATION NO. : 14/899653
DATED : April 9, 2019
INVENTOR(S) : Alain Lagrange et al.

It is certified that error appears in the above-identified patent and that said Letters Patent is hereby corrected as shown below:

In the Claims

Column 43, Line 18, second compound, change "diocol" to -- dioxol --

Column 43, between Lines 50 and 55, second formula, please replace with the formula below:

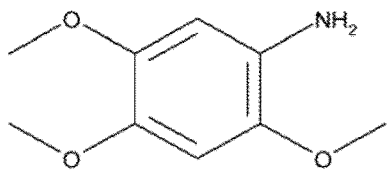

Column 45, Line 48, change "thean" to -- ethan --

Column 46, Line 50, change "Natural" to -- Naturel --

Signed and Sealed this
Nineteenth Day of November, 2019

Andrei Iancu
*Director of the United States Patent and Trademark Office*